United States Patent
Keach et al.

(10) Patent No.: US 11,779,468 B2
(45) Date of Patent: Oct. 10, 2023

(54) IMPLANT EXTRACTOR

(71) Applicant: Shukla Medical, St. Petersburg, FL (US)

(72) Inventors: Nicholas Christopher Keach, Lutz, FL (US); Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 120 days.

(21) Appl. No.: 17/301,689

(22) Filed: Apr. 12, 2021

(65) Prior Publication Data
US 2021/0315713 A1    Oct. 14, 2021

Related U.S. Application Data

(60) Provisional application No. 63/009,618, filed on Apr. 14, 2020.

(51) Int. Cl.
*A61F 2/46* (2006.01)

(52) U.S. Cl.
CPC .......... *A61F 2/4603* (2013.01); *A61F 2/4607* (2013.01); *A61F 2002/4619* (2013.01); *A61F 2002/4622* (2013.01); *A61F 2002/4627* (2013.01)

(58) Field of Classification Search
CPC .................. A61F 2/4603; A61F 2/4607; A61F 2002/4622
See application file for complete search history.

(56) References Cited

U.S. PATENT DOCUMENTS

| 5,476,466 A | * | 12/1995 | Barrette | A61F 2/4607 606/86 R |
| 5,534,006 A | * | 7/1996 | Szabo | A61F 2/4607 606/100 |
| 6,033,405 A | * | 3/2000 | Winslow | A61F 2/4611 606/86 R |

(Continued)

FOREIGN PATENT DOCUMENTS

EP    0550118 B1    7/1996

OTHER PUBLICATIONS

Extended European Search Report dated Aug. 20, 2021 in EP Application No. 21168143.2.
(Continued)

*Primary Examiner* — Matthew J Lawson
(74) *Attorney, Agent, or Firm* — Kim IP Law Group LLC

(57) ABSTRACT

An implant extractor including a shaft body and a telescoping push rod extending from the shaft body. An adjustor is engaged with the telescoping push rod for adjusting a length of the telescoping push rod. A support arm extends laterally away from the shaft body and a jaw assembly extends from the support arm. The jaw assembly includes a jaw moveable between a locking position and an unlocking position, and a rocker arm operatively engaged with the telescoping push rod and the jaw. The implant extractor provides a line of force spaced from and substantially parallel to an implant to be extracted. As a consequence, there is substantial clearance for an extension handle such as a C-frame or the like which is oftentimes needed to dislodge the implant from surrounding bone. In addition, the implant extractor is capable of gripping a wide range of sizes of hip stem implant trunnions.

24 Claims, 26 Drawing Sheets

(56) References Cited

U.S. PATENT DOCUMENTS

| | | | |
|---|---|---|---|
| 6,322,564 B1* | 11/2001 | Surma | A61F 2/4607 |
| | | | 606/89 |
| 8,398,650 B1 | 3/2013 | Burgi | |
| 8,603,100 B2 | 12/2013 | Muller | |
| 2006/0200162 A1* | 9/2006 | Fading | A61B 17/157 |
| | | | 606/88 |
| 2008/0221576 A1* | 9/2008 | Keller | A61F 2/4607 |
| | | | 606/151 |
| 2008/0262503 A1* | 10/2008 | Muller | A61F 2/4612 |
| | | | 606/99 |
| 2010/0331902 A1 | 12/2010 | Biegun | |
| 2012/0253469 A1* | 10/2012 | Collins | A61F 2/4603 |
| | | | 623/23.15 |
| 2014/0207123 A1* | 7/2014 | Mueller | A61F 2/4607 |
| | | | 606/1 |
| 2016/0270929 A1* | 9/2016 | Sweitzer | A61F 2/461 |
| 2020/0214853 A1* | 7/2020 | Sweitzer | A61F 2/4603 |
| 2021/0290411 A1* | 9/2021 | Gosik-Wolfe | A61F 2/4612 |
| 2023/0000644 A1* | 1/2023 | Kiska | A61F 2/4603 |

OTHER PUBLICATIONS

European Patent Office—Communication Pursuant to Article 94(3) EPC, dated Mar. 3, 2023 in the Counterpart European Patent Application No. 21 168 143.2.

* cited by examiner

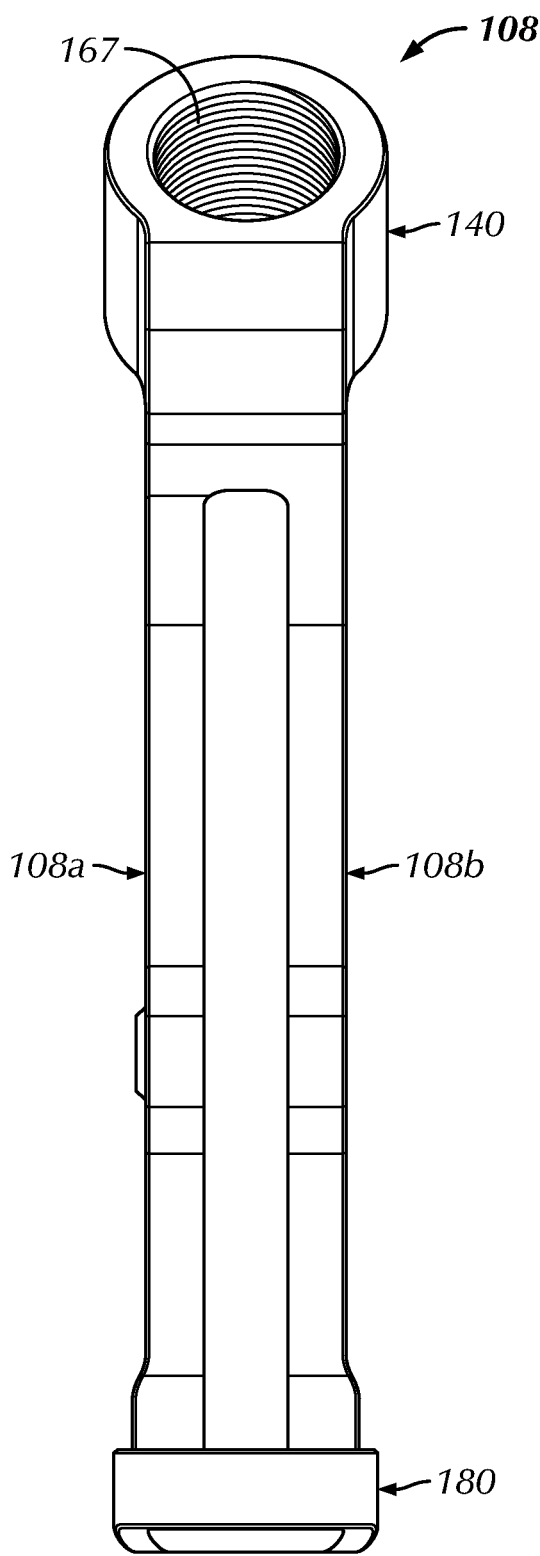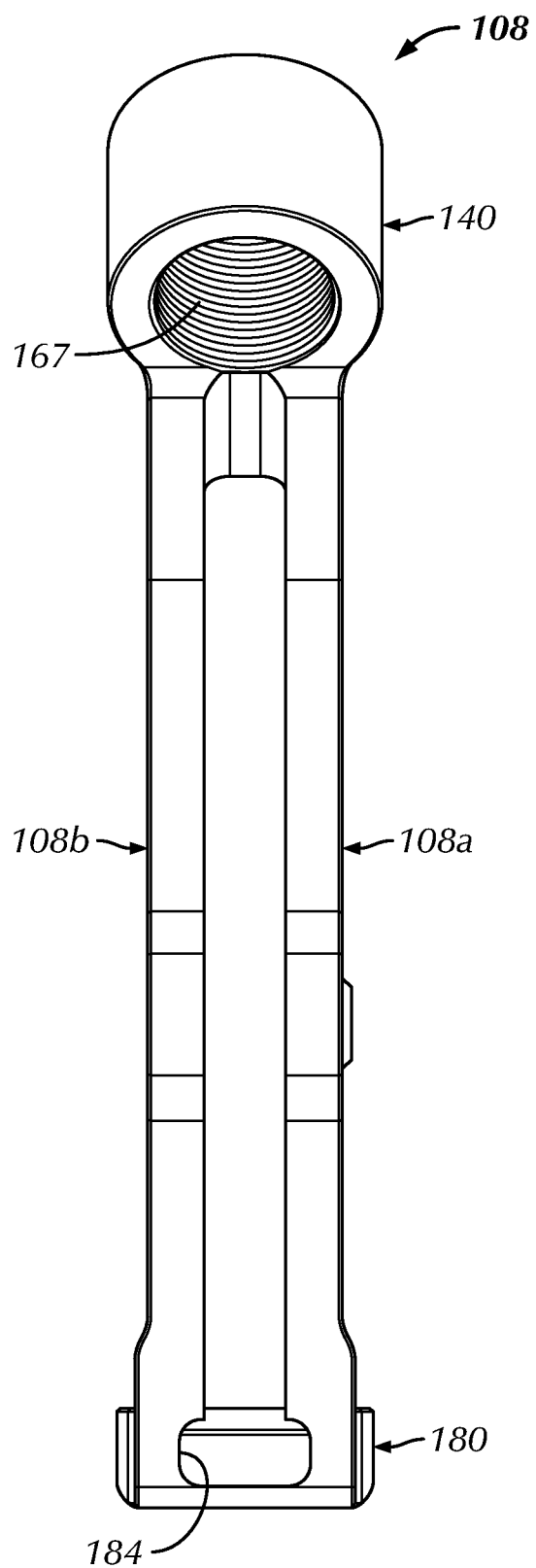
FIG. 16D     FIG. 16E

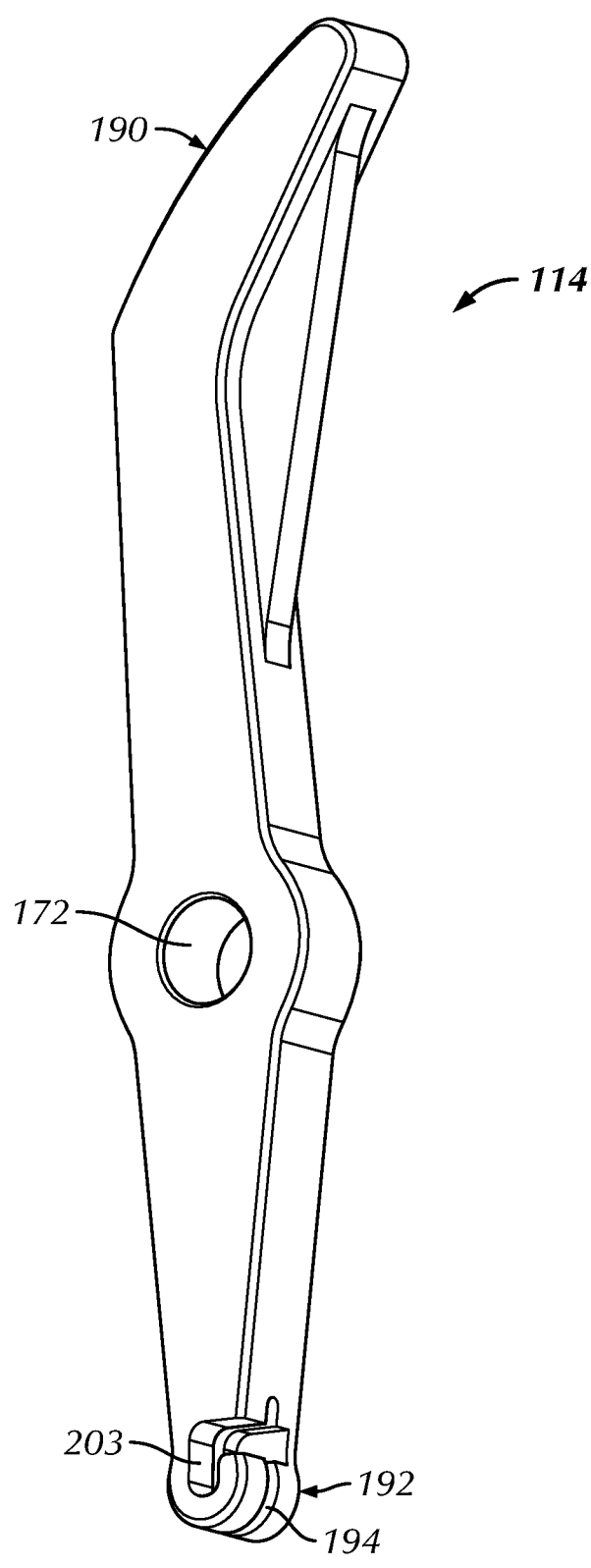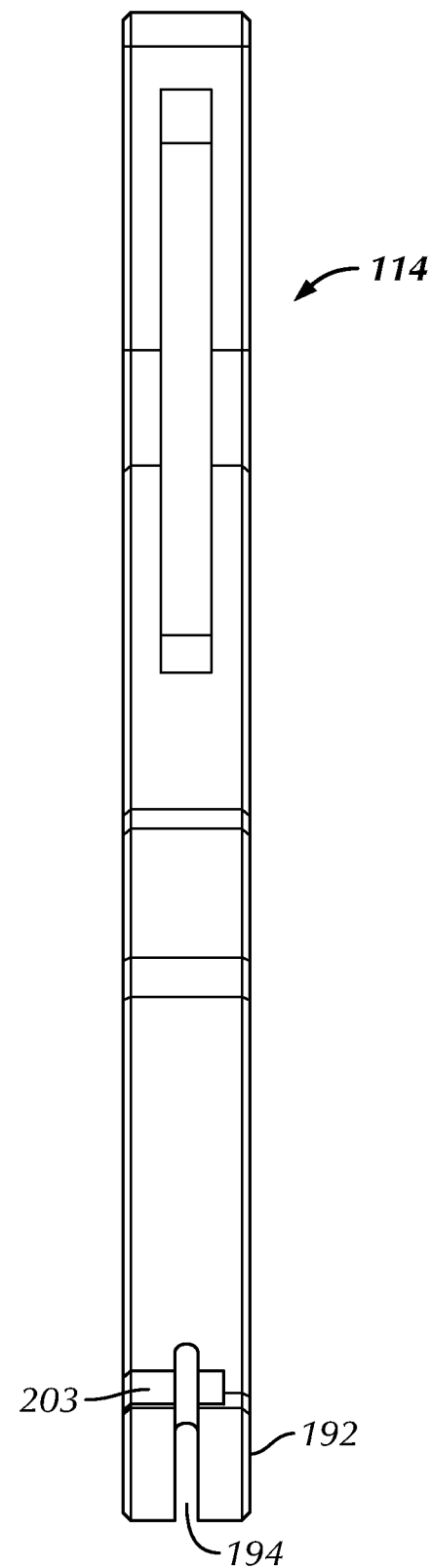
*FIG. 17B*      *FIG. 17C*

IMPLANT EXTRACTOR

CROSS-REFERENCE TO RELATED APPLICATION

This application claims the benefit under 35 U.S.C. § 119(e) to U.S. Provisional Application No. 63/009,618, filed Apr. 14, 2020, and entitled "Anterior Hip Extractor," the entire disclosure of which is hereby incorporated by reference for all purposes.

BACKGROUND OF THE DISCLOSURE

The exemplary embodiments of present invention relate generally to a surgical extraction tool and, more specifically, to a tool for extracting an implant from bone including, without limitation, a hip stem implant.

A typical anterior hip stem implant extractor tool has a longitudinal axis generally coextensive with the hip stem implant to be extracted. As a result, this allows the device to clear the patient's body which is necessary due to the typical orientation the patient's body needs to be placed in to perform the surgery via the direct anterior approach. In this approach, the incision is made on the anterior plane of the hip which differs from the posterior-lateral approach. Thus, in order to align the hip stem with an opening for extraction, the patient's leg needs to be dislocated and bent posterior or to the rear to allow access. Otherwise, the patient's midsection would prevent the hip stem from being extracted. The patient's leg can only be positioned to such a maximum angle dependent on the patient's anatomy, thus the necessary surgical instrumentation to remove a patient's hip stem requires an offset to clear the patient's belly. Such an offset is not needed for a posterior lateral approach because the patient can easily be bent forward at the hip in a regular anatomical position and have the hip stem extracted posteriorly, i.e., out the rear. The direct anterior approach is gaining popularity because significantly less soft tissue needs to be severed to allow for the surgery when compared to the posterior-lateral approach, which in turn, allows for a considerable reduction in recovery time for the patient. Indeed, in some cases the anterior approach allows patients to be walking on their own the day after surgery.

BRIEF SUMMARY OF THE DISCLOSURE

In accordance with an exemplary embodiment there is provided an implant extractor comprising a shaft body and a telescoping push rod extending from the shaft body. An adjustor is engaged with the telescoping push rod for adjusting a length of the telescoping push rod. A support arm extends laterally from the shaft body and a jaw assembly extends from the support arm. The jaw assembly includes a jaw moveable between a locking position and an unlocking position, and a rocker arm operatively engaged with the telescoping push rod and the jaw.

According to an aspect, the implant extractor further includes a cam lock operatively engaged with the telescoping push rod. According to another aspect, the cam lock includes a cam housed within the shaft body, and a lever extending from the cam. According to another aspect, the telescoping push rod is housed within the shaft body. According to another aspect, a distal end of the telescoping push rod extends past a distal end of the shaft body. According to another aspect, the telescoping push rod is moveable relative to the housing. According to another aspect, the telescoping push rod includes a distal rod segment having a planar side. According to another aspect, the telescoping push rod includes a proximal rod segment having a rotation limiter.

According to another aspect, the adjustor is positioned about a distal end of the shaft body. According to another aspect, the adjustor includes an adjustment knob engaged with the telescoping push rod. According to another aspect, the support arm extends from a distal end of the adjustor. According to another aspect, the support arm has a longitudinal axis that extends from a longitudinal axis of the shaft body at an angle of about 100 to 170 degrees. According to another aspect, the support arm has a length of about 10 to 400 mm.

According to another aspect, the jaw extends from a distal end of the support arm. According to another aspect, the jaw is a sliding jaw. According to another aspect, the jaw assembly includes a central passageway having a longitudinal axis substantially parallel to a longitudinal axis of the support arm. According to another aspect, the implant extractor further includes a gripping insert configured to be received in the central passageway. According to another aspect, the gripping insert includes grip enhancing structure. According to another aspect, the gripping insert is annular with a lateral opening for receiving the jaw.

According to another aspect, the rocker arm is pivotably connected to the support arm. According to another aspect, the rocker arm has a rocker arm ratio of about 1.5:1 to 8:1. According to another aspect, the rocker arm has at least one arm of about 10 to 100 mm. According to another aspect, the implant extractor further comprises a tool connector extending laterally away from the shaft body in a direction substantially opposite from the direction the support arm is extending laterally away from the shaft body.

In accordance with another exemplary embodiment there is provided an implant extractor comprising a shaft body and a tool connecter extending laterally away from a proximal end of the shaft body. A telescoping push rod is mounted within and extends from the shaft body. The telescoping push rod includes a proximal rod segment and distal rod segment moveable relative to the proximal rod segment. A cam lock is mounted within the shaft body for engaging a proximal end of the telescoping push rod. An adjustor is mounted to a distal end of the shaft body. The adjustor includes an adjustment knob engaged with the telescoping push rod for adjusting a length of the telescoping push rod. A support arm is mounted to a distal end of the adjustor and extends laterally away from the shaft body. A jaw assembly extends from a distal end of the support arm. The jaw assembly includes a jaw moveable between a locking position and an unlocking position, and a rocker arm mounted to the support arm and operatively engaged with the telescoping push rod and the jaw.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

FIG. 16D is a front view of the support arm of FIG. 16A;

FIG. 16E is a rear view of the support arm of FIG. 16A;

FIG. 17B is a rear perspective view of the rocker arm of FIG. 17A;

FIG. 17C is a rear view of the rocker arm of FIG. 17A;

DETAILED DESCRIPTION OF THE DISCLOSURE

Figure 1:
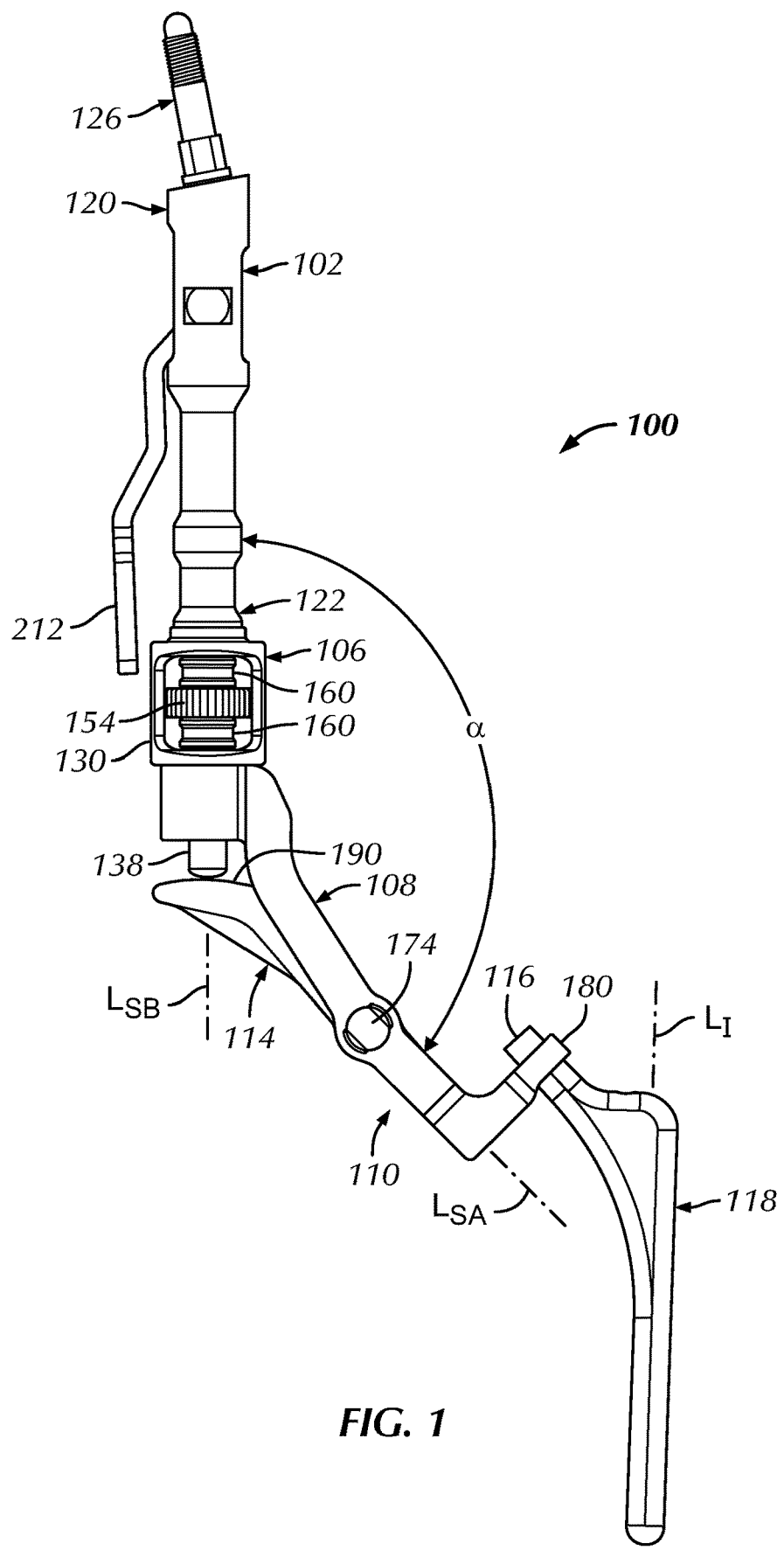
FIG. 1 is side view of an implant extractor in accordance with an exemplary embodiment of the subject disclosure shown clamping a hip stem implant.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2:
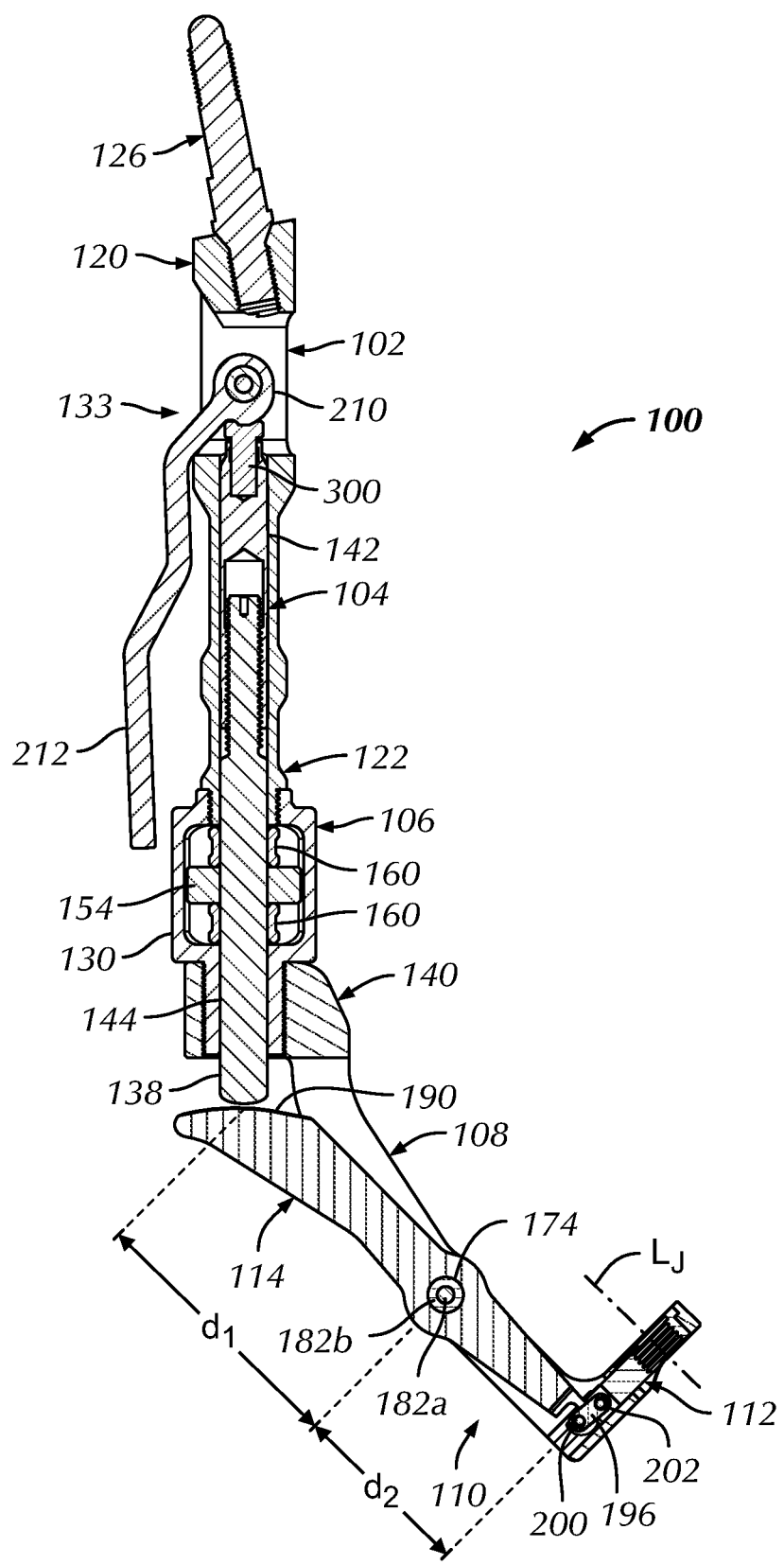
FIG. 2 is a side cross-sectional view of the implant extractor of FIG. 1.

Referring now to the drawings, FIGS. 1-6 illustrate an implant extractor 100 in accordance with an exemplary embodiment of the present disclosure. As best shown in FIG. 2, the implant extractor 100 comprises a shaft body 102, a telescoping push rod 104 extending from the shaft body, an adjuster, a support arm, and a jaw assembly. The adjustor 106 is engaged with the telescoping push rod for adjusting a length of the telescoping push rod. The support arm 108 extends laterally from the shaft body and the jaw assembly 110 extends from the support arm. The jaw assembly includes a jaw 112 moveable between a locking position and an unlocking position, and a rocker arm 114 operatively engaged with the telescoping push rod and the jaw. As described in greater detail below, the jaw assembly is operable to releasably clamp to an implant e.g., a trunnion 116 of a hip stem implant 118 (FIG. 1), wherein the hip stem implant defines a longitudinal axis "$L_I$."

Figure 6:
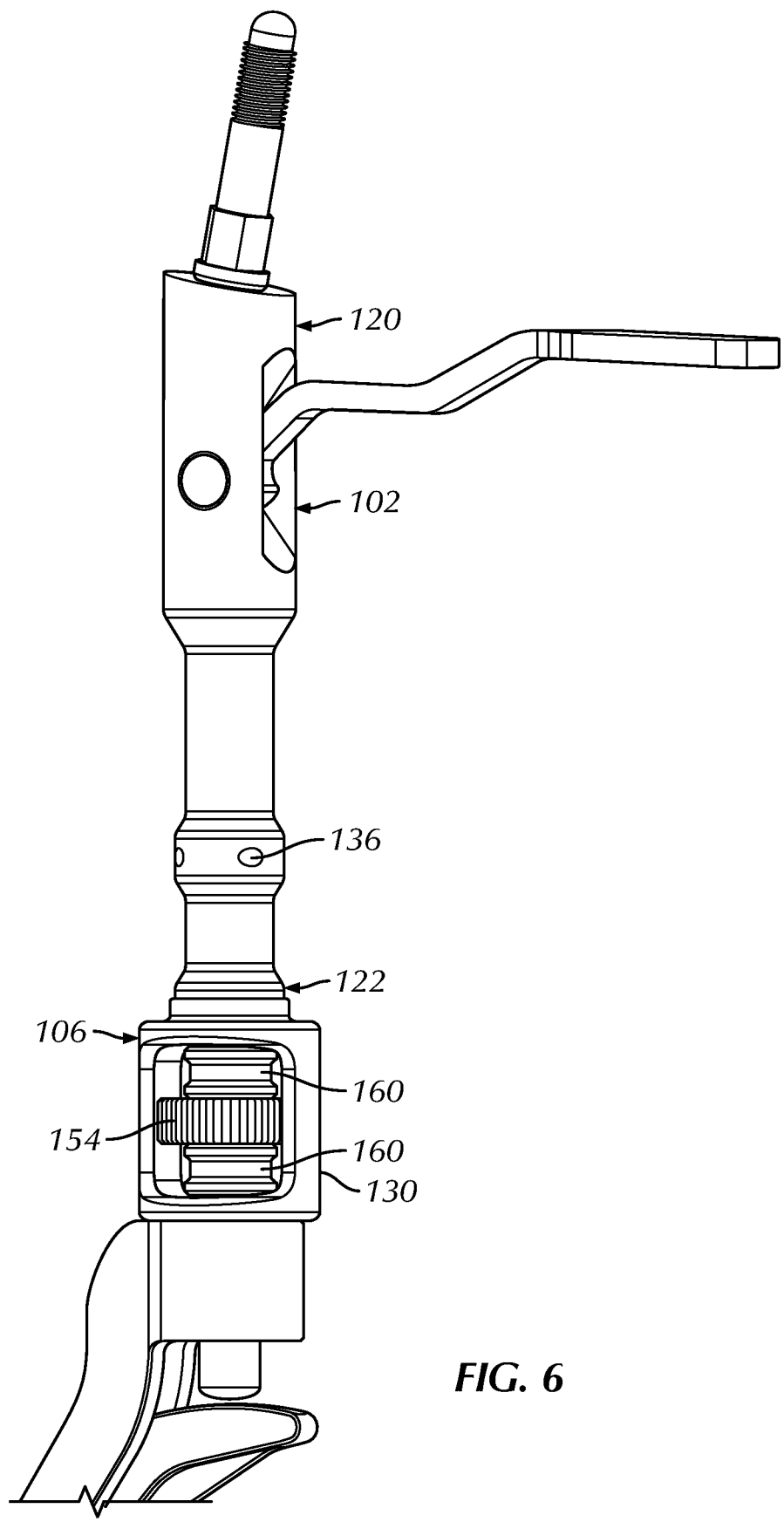
FIG. 6 is a side view of a portion of the implant extractor of FIG. 1 with a cam lever thereof shown in a non-camming position.
Figure 7A:
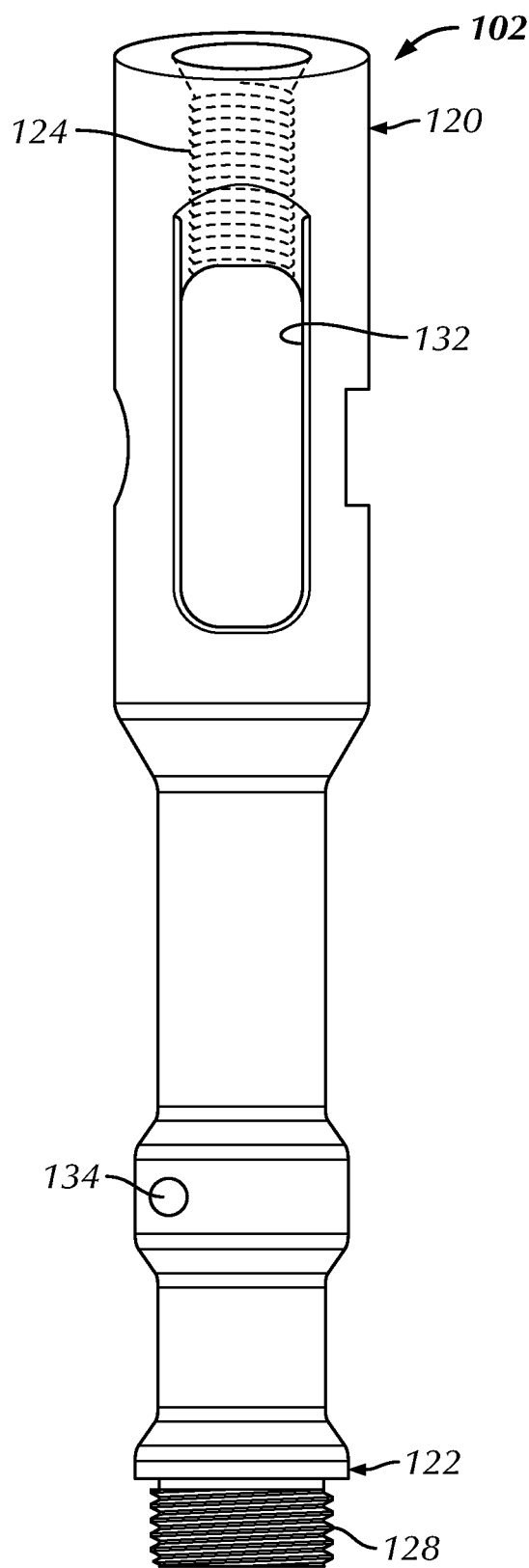
FIG. 7A is a side view of a shaft body of the implant extractor of FIG. 1.
Figure 7B:
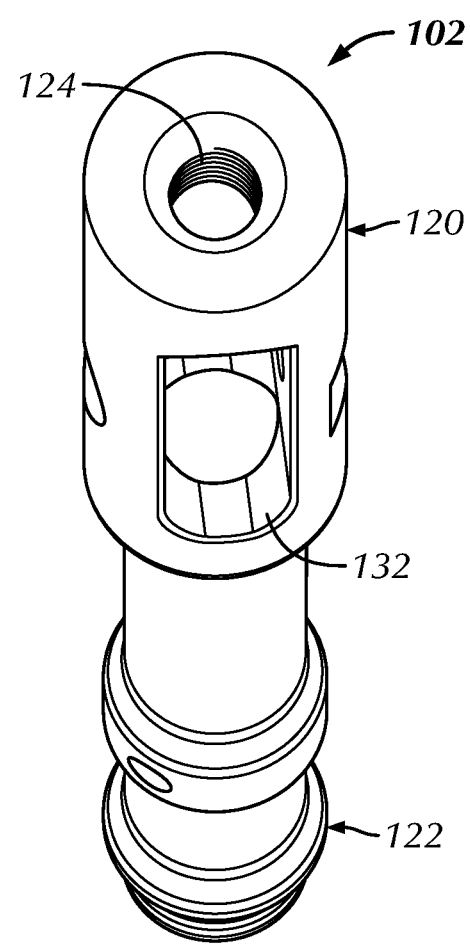
FIG. 7B is a top perspective view of the shaft body of FIG. 7A.
Figure 13A:
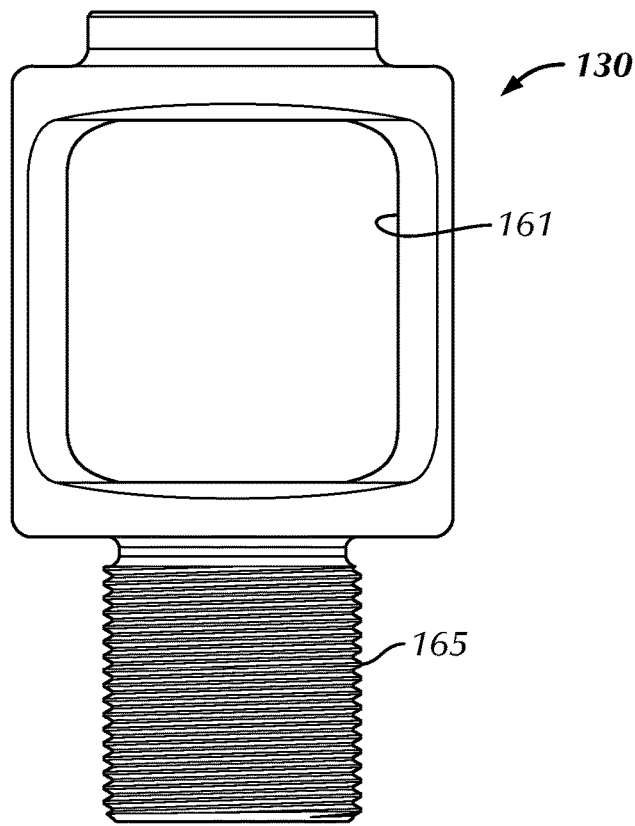
FIG. 13A is a side view of an adjustor cage of the implant extractor of FIG. 1.
Figure 13B:
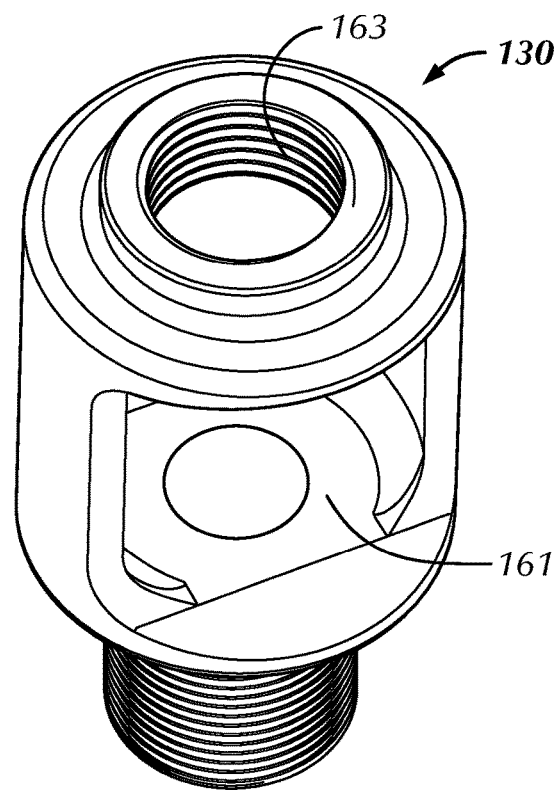
FIG. 13B is a top perspective view of the adjustor cage of FIG. 13A.

Referring to FIGS. 7A and 7B, there is shown an exemplary construction of the shaft body 102. The shaft body is a hollow elongated member having a proximal end 120 and a distal end 122 and defining a longitudinal axis "$L_{SB}$" (FIG. 1). According to an aspect, the lateral offset of $L_{SB}$ from $L_I$ is approximately four inches to provide room for the implant extractor to avoid contact with exposed soft tissue during a surgical procedure. However, the lateral offset can alternatively be more or less than 4 inches, e.g., 3, 5, 6, 7, and 8 inches or more. At a proximal tip of the shaft body, there is provided an internally threaded opening 124 for threadedly receiving a tool connector 126 (FIG. 8), described below. At a distal tip of the shaft body, there is provided an externally threaded projection 128 for threadedly engaging a cage 130 of the adjustor 106 (FIGS. 13A and 13B). Adjacent the proximal end 120, the shaft body includes a transverse through opening 132 for receiving a cam lock 133 (FIG. 9), described below. Between the through opening 132 and the distal end 122 the shaft body includes a through bore 134 extending transverse to the longitudinal axis of the shaft body for receiving a pin 136 (FIG. 6).

Figure 10:
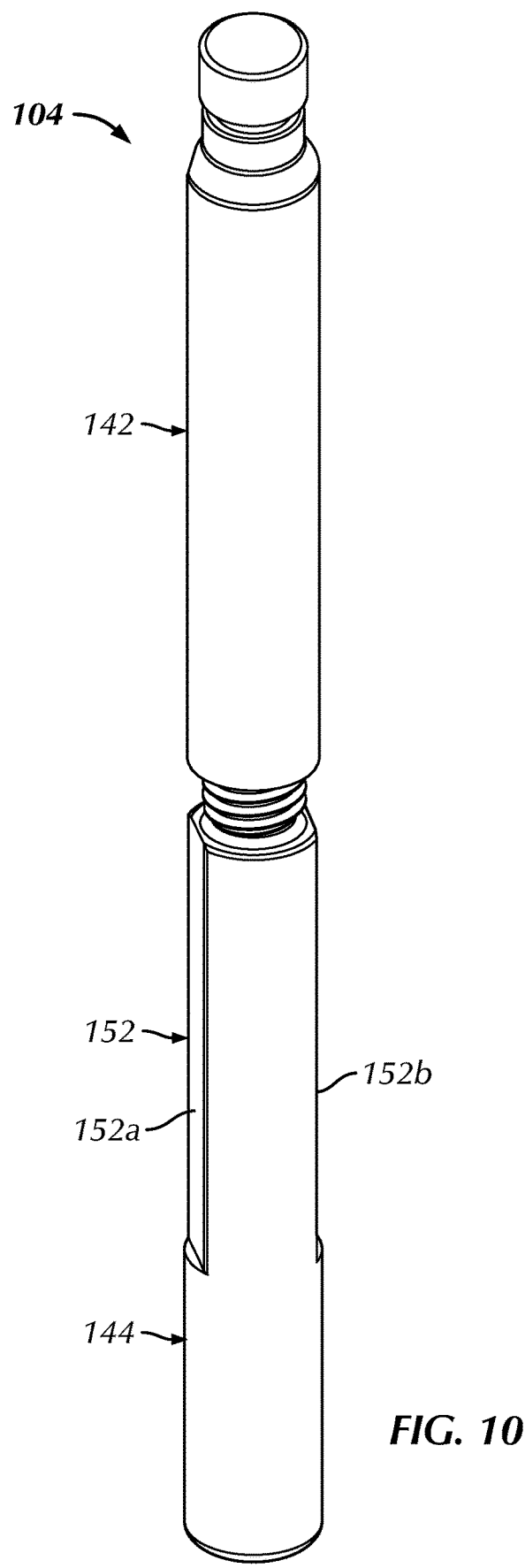
FIG. 10 is a perspective view of a telescoping push rod of the implant extractor of FIG. 1.
Figure 11:
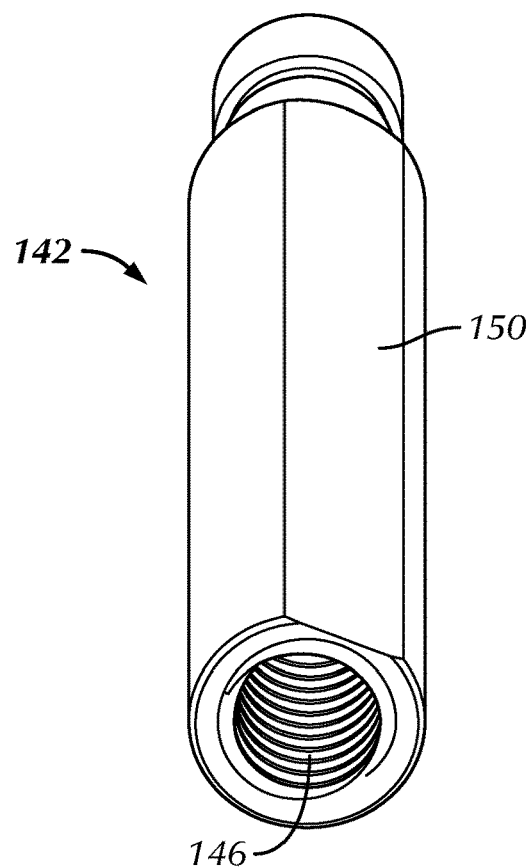
FIG. 11 is a perspective view of a proximal rod segment of the telescoping push rod of FIG. 10.
Figure 12:
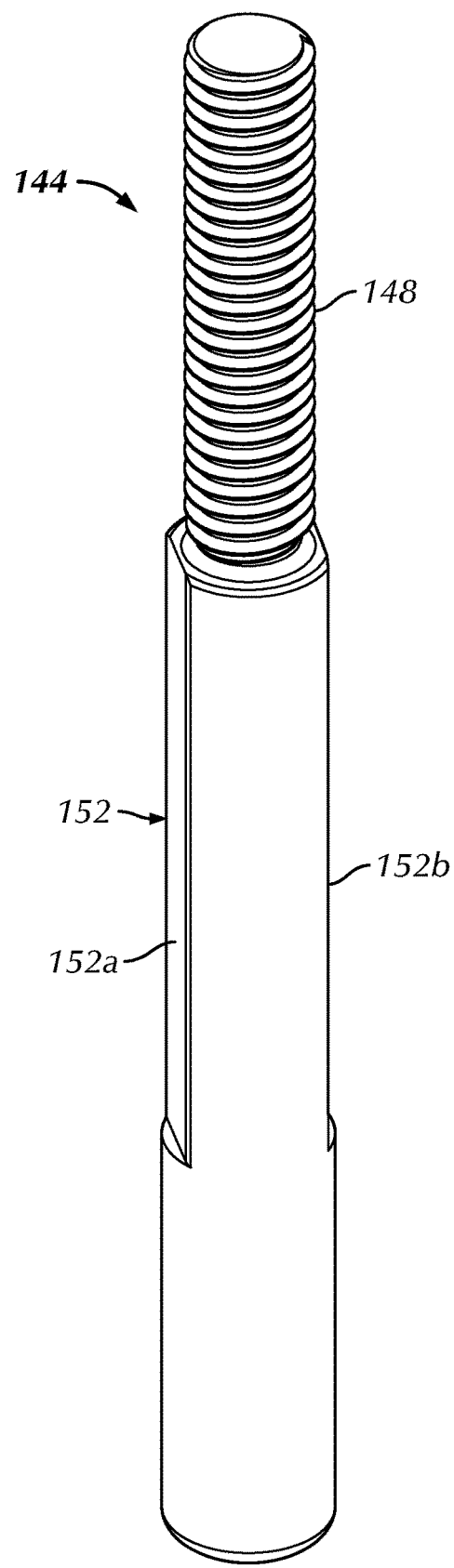
FIG. 12 is a perspective view of a distal rod segment of the telescoping push rod of FIG. 10.

As best shown in FIG. 2, the telescoping push rod 104 is housed within the shaft body 102 and is moveable relative to the shaft body. A distal end 138 of the telescoping push rod extends past the distal end of the shaft body, the adjustor 106 and a junction portion 140 of the support arm 108 (FIGS. 16A-16E). The construction of the telescoping push rod 104 is best shown in FIGS. 10-12. The telescoping push rod includes a proximal rod segment 142 and a distal rod segment 144 moveable relative to the proximal rod segment. According to an aspect, a distal end of the proximal rod segment is provided with an internally threaded bore 146 that threadedly receives a threaded shaft 148 at a proximal end of the distal rod segment. Alternatively, the distal end of the proximal rod segment can be provided with a threaded shaft to be received with in a threaded bore and the distal rod segment.

Referring to FIG. 11, the proximal rod segment 142 has rotation limiter 150 in the form of a planar side that is configured to be contacted by the pin 136 (FIG. 6) which prevents rotation but permits translation e.g., axial translation of the proximal rod segment during operation of the implant extractor. Referring to FIGS. 10 and 12, the distal rod segment 144 has at least one planar side 152, and preferably a pair of oppositely facing planar sides 152a and 152b, the function of which is described below.

As shown in FIGS. 1-3 and 6, the adjustor 106 is positioned about the distal end 122 of the shaft body 102. The adjustor includes an adjustment knob 154 engaged with the telescoping push rod 104 for adjusting a length of the telescoping push rod.

Figure 14:
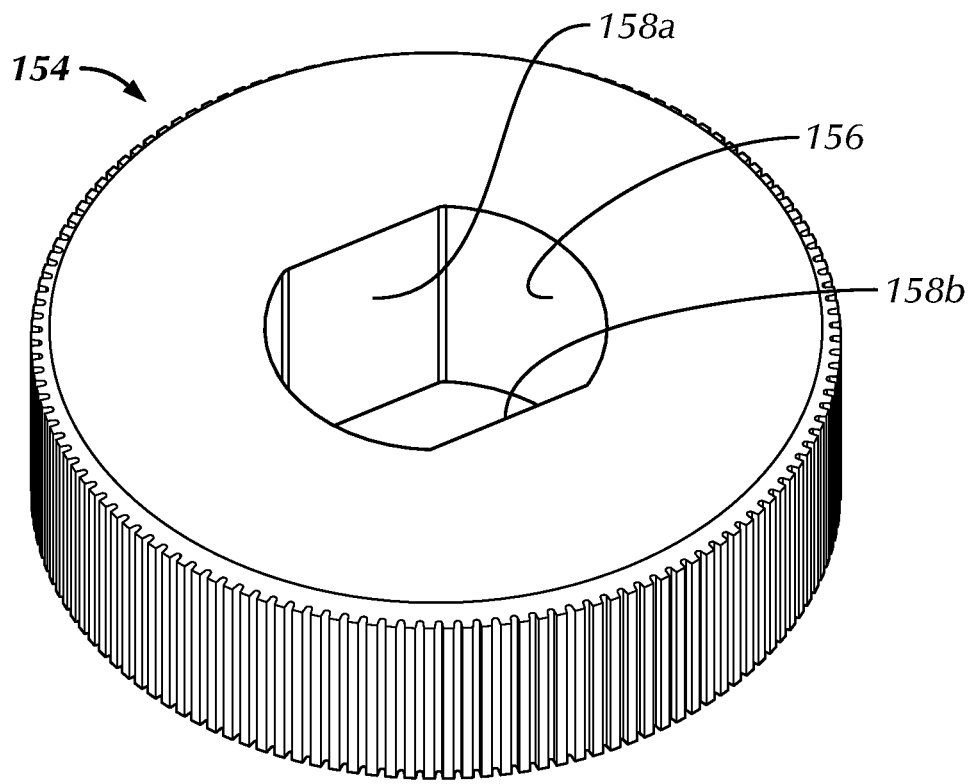
FIG. 14 is a perspective view of an adjuster of the implant extractor of FIG. 1.

Referring to FIG. 14, the adjustment knob 154 includes a central opening 156 defined by a pair of planar surfaces 158a, 158b for slidably receiving the oppositely facing planar sides 152a, 152b of the distal rod segment of the telescoping push rod 104. At its periphery, the adjustment knob can include splines, knurling or other grip-enhancing structure to prevent slipping of a user's fingers from the adjustment knob during turning thereof.

Figure 15:
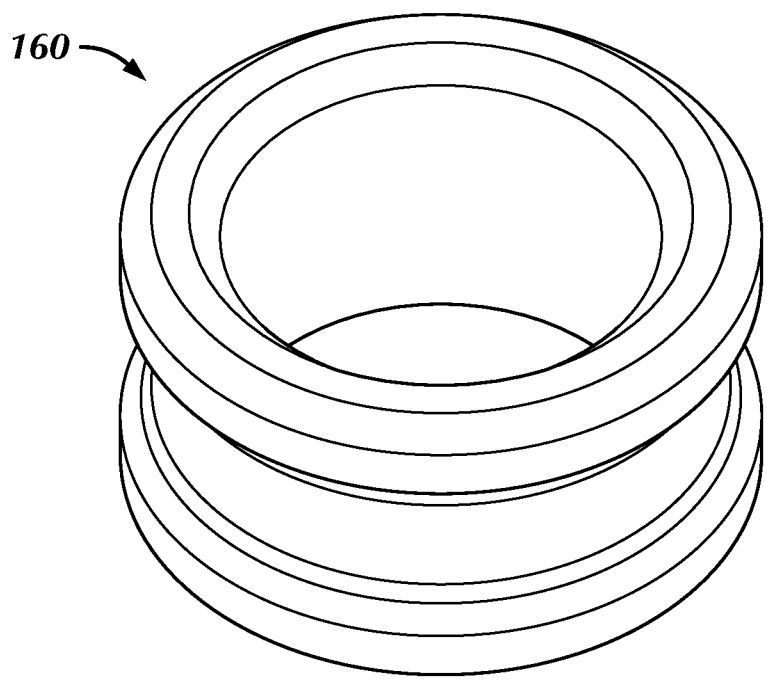
FIG. 15 is a perspective view of an adjuster spacer of the implant extractor of FIG. 1.

The adjustor 106 further includes a pair of spacers 160 (FIG. 3) situated on opposite sides of the adjustment knob 154 and contacting the adjustment knob and the adjustor cage 130 for preventing axial movement of the adjustment knob during rotation thereof. An enlarged view of a spacer 160 is shown in FIG. 15.

Referring to FIGS. 13A and 13B, the cage 130 of the adjustor includes at least one opening 161 for permitting a user's fingers to access and rotate the adjustment knob. The opening 161 is preferably a through hole through the cage from one lateral side to an opposite lateral side. The proximal end of the cage is internally threaded 163 to threadedly receive the threaded distal end of the shaft body (FIG. 7A), and the distal end 165 of the cage is externally threaded to threadedly engage internal threading 167 of the junction portion 140 of the support arm (FIGS. 16B-16E).

Figure 4:
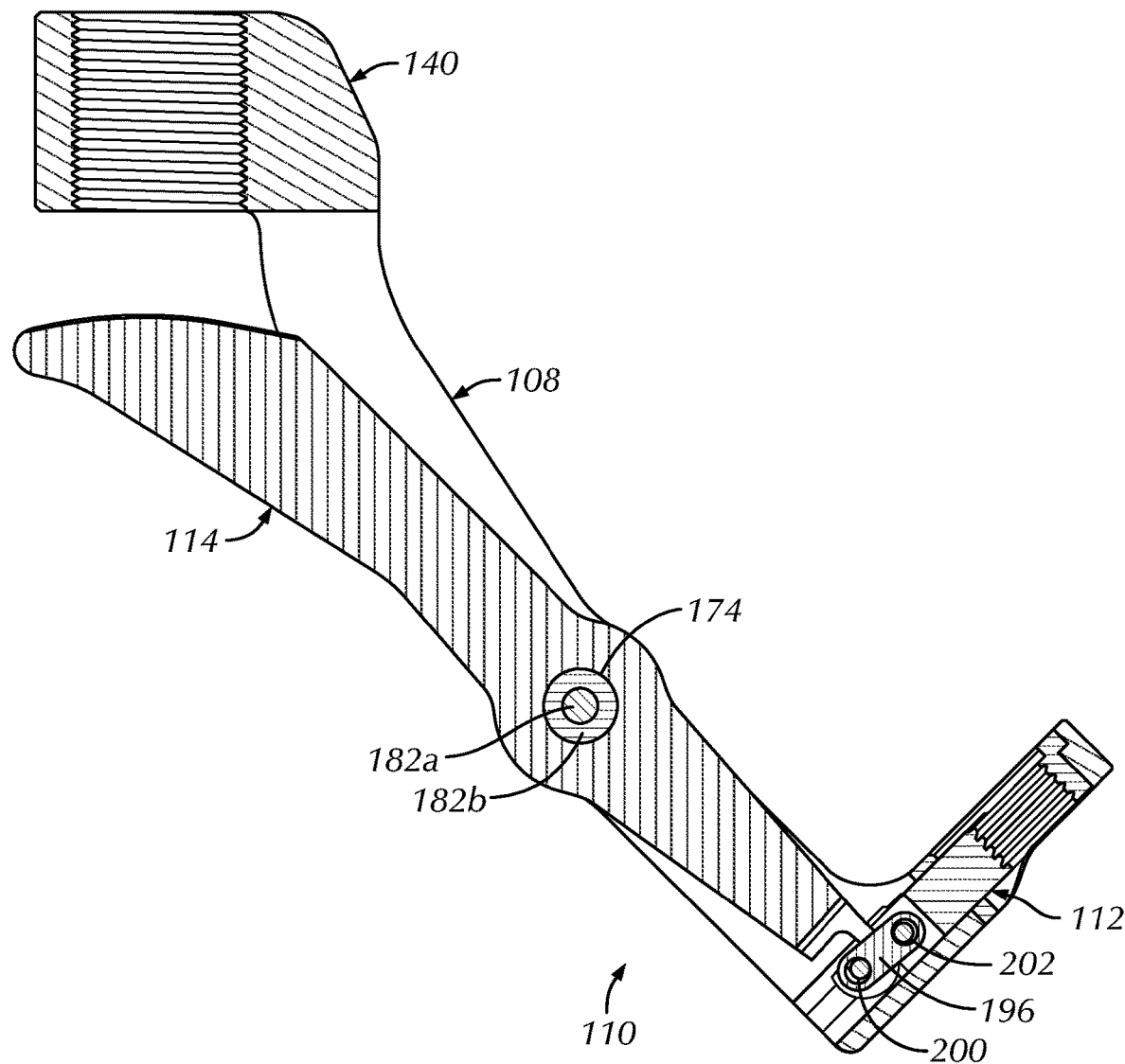
FIG. 4 is a side cross-sectional view of a lower portion of the implant extractor of FIG. 1.

As shown in FIGS. 1, 2 and 4, the support arm 108 extends from about a distal end of the adjustor 106, and more specifically from a bottom end of the adjuster. Referring to FIG. 1, the support arm 108 has a longitudinal axis "$L_{SA}$" that traverses the longitudinal axis $L_{SB}$ of the shaft body 102 at an angle α of about 100 to 170 degrees, including 95, 105, 110, 115, 120, 125, 130, 135, 140, 145, 150, 155, 160, 165 and 175 degrees. The support arm has a length of about 10 to 400 mm, including 20, 30, 40, 50, 60, 70, 80, 90, 100, 120, 140, 160, 180, 200, 220, 240, 260, 280, 300, 320, 340, 360 and 380 mm, or greater than 400 mm.

Figure 16A:
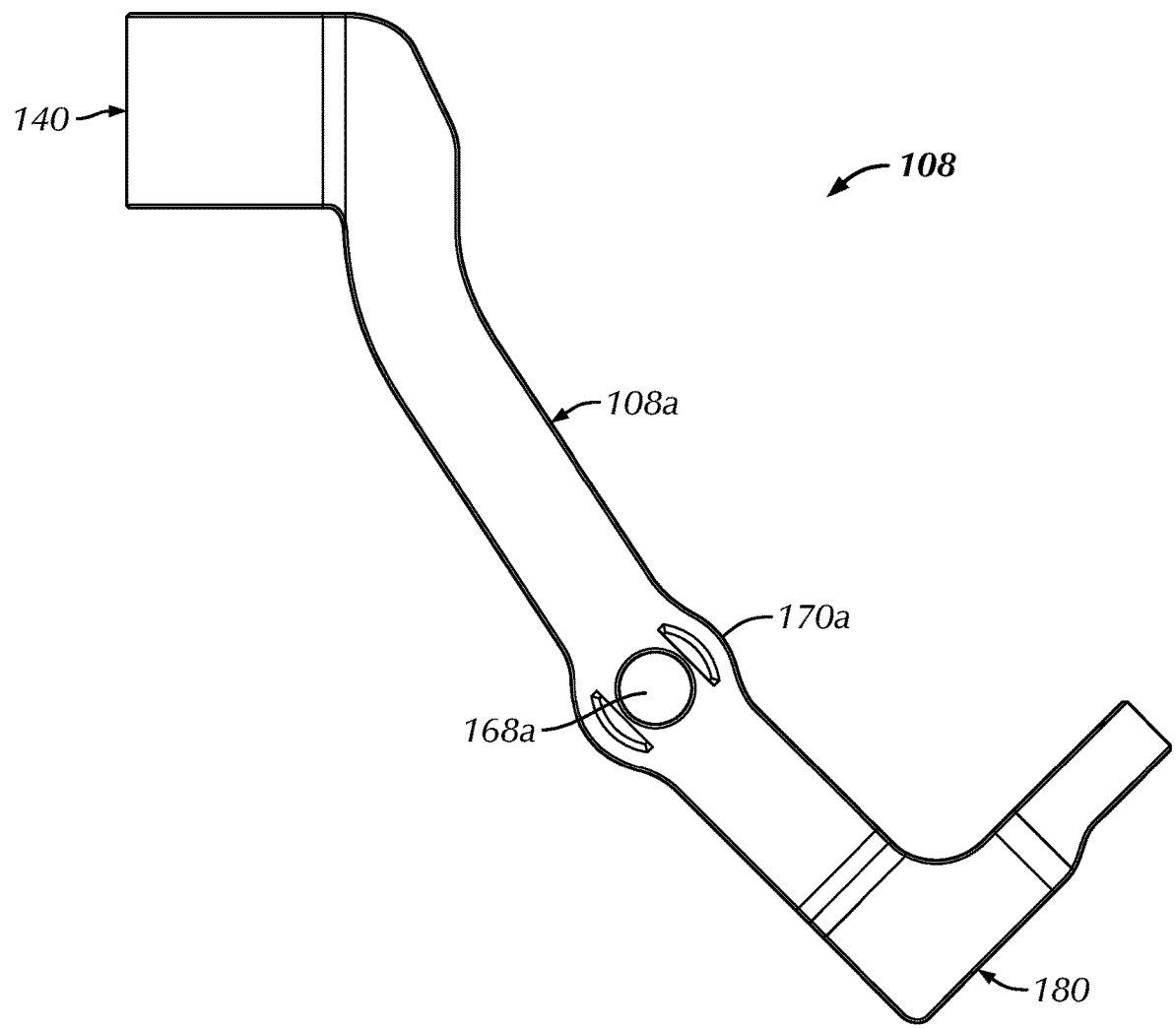
FIG. 16A is a side view of a support arm of the implant extractor of FIG. 1.
Figure 16B:
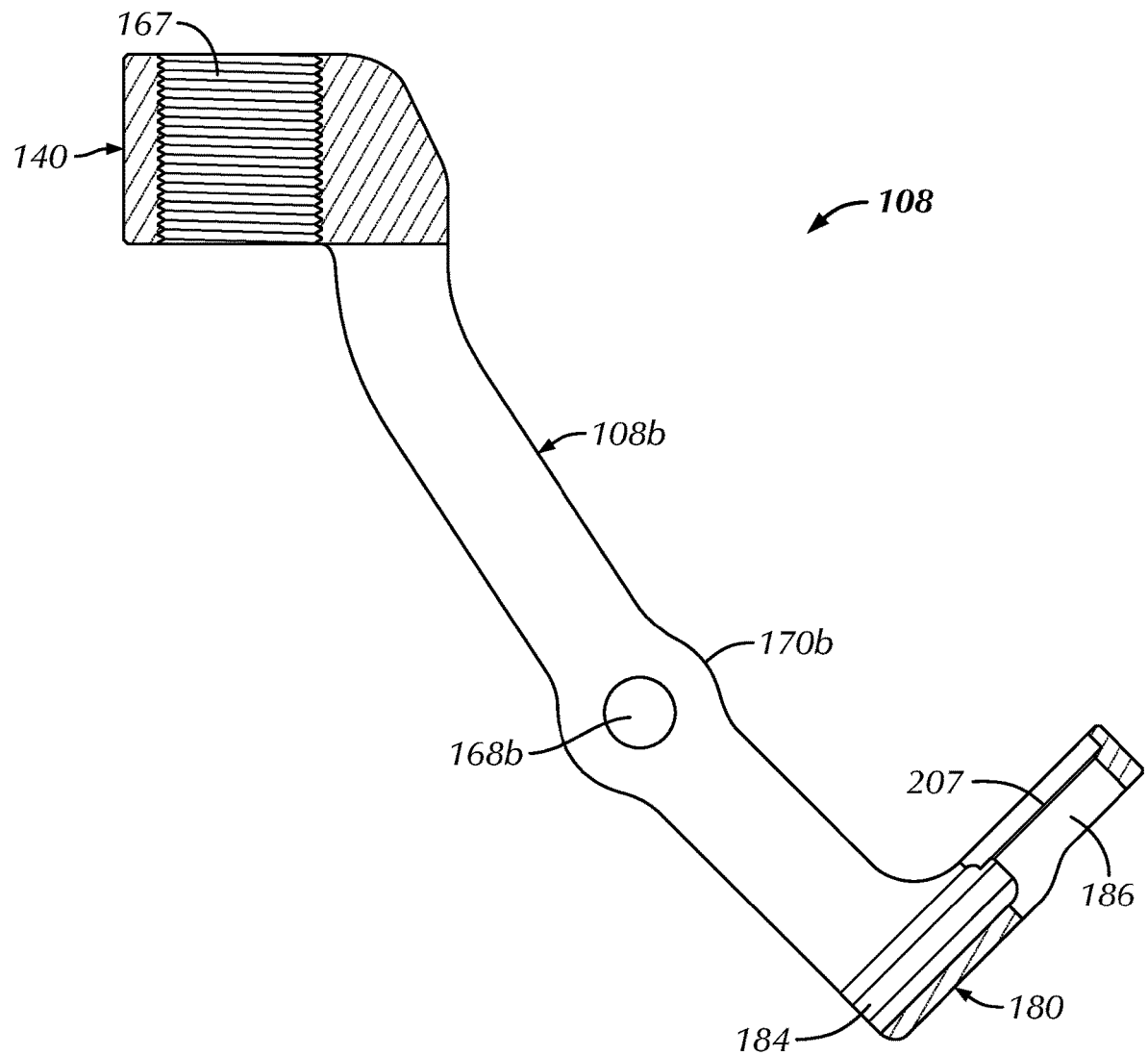
FIG. 16B is a side cross-sectional view of the support arm of FIG. 16A.
Figure 16C:
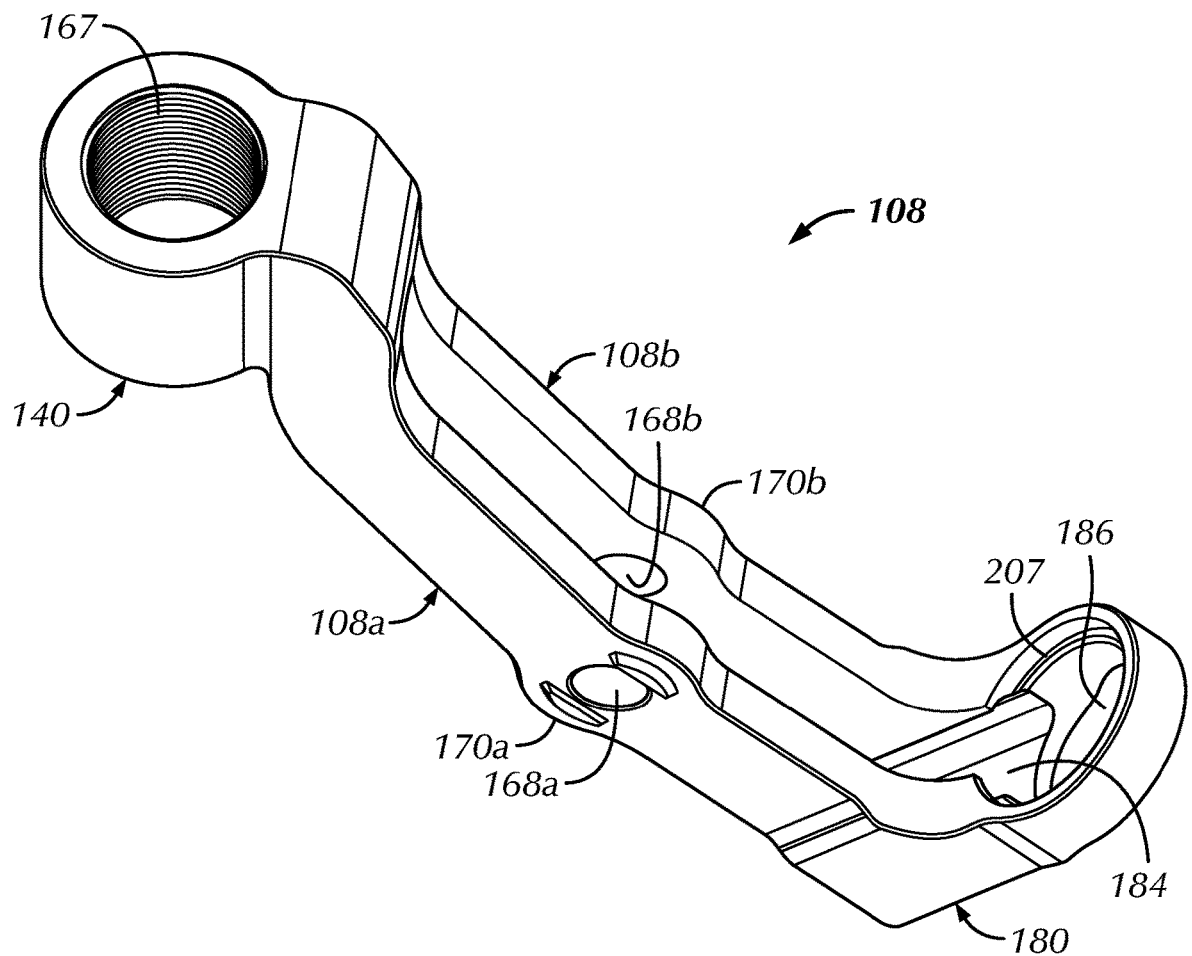
FIG. 16C is a perspective view of the support arm of FIG. 16A.
Figure 17A:
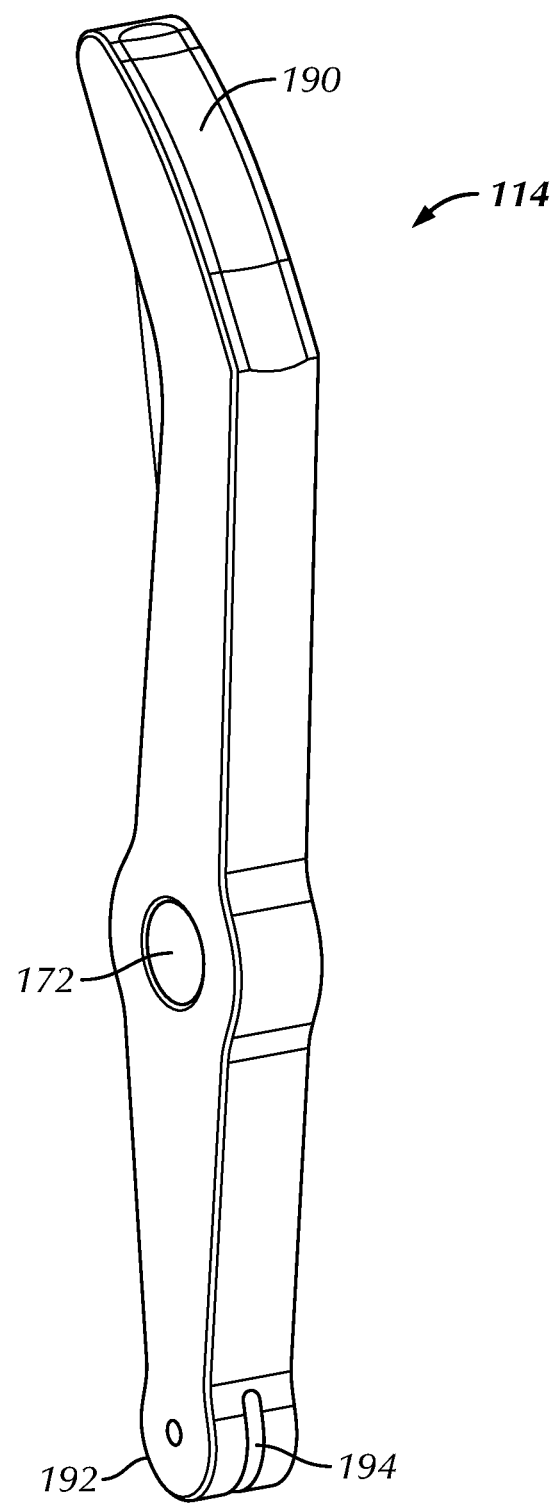
FIG. 17A is a front perspective view of a rocker arm of the implant extractor of FIG. 1.

The support arm 108 can be fabricated from two or more pieces. However, for optimum rigidity, the support arm is preferably a unitary member as illustrated in FIGS. 16A-16E. The support arm is preferably constructed as a pair of parallel support arm segments 108a and 108b that extend downwardly from the junction portion 140. Aligned through bores 168a and 168b are provided at intermediate portions 170a and 170b of the support arm segments. The aligned through bores 168a, 168b are also aligned with a through bore 172 of the rocker arm 114 (FIGS. 17A-17C). A pivot pin 174 (FIGS. 1, 2 and 4) passes through the aligned through bores 168a, 168b and the through bore 172 whereby the rocker arm 114 is pivotably connected to the support arm between the support arm segments. According to an aspect, the pivot pin 174 comprises threadedly connected male and female pin parts 182a, 182b, respectively, (FIGS. 2 and 4). Distal ends of the support arm segments 108a, 108b are joined to a jaw carrier 180 (FIGS. 16A-16E) constructed to slidingly support the jaw 112.

Figure 5:
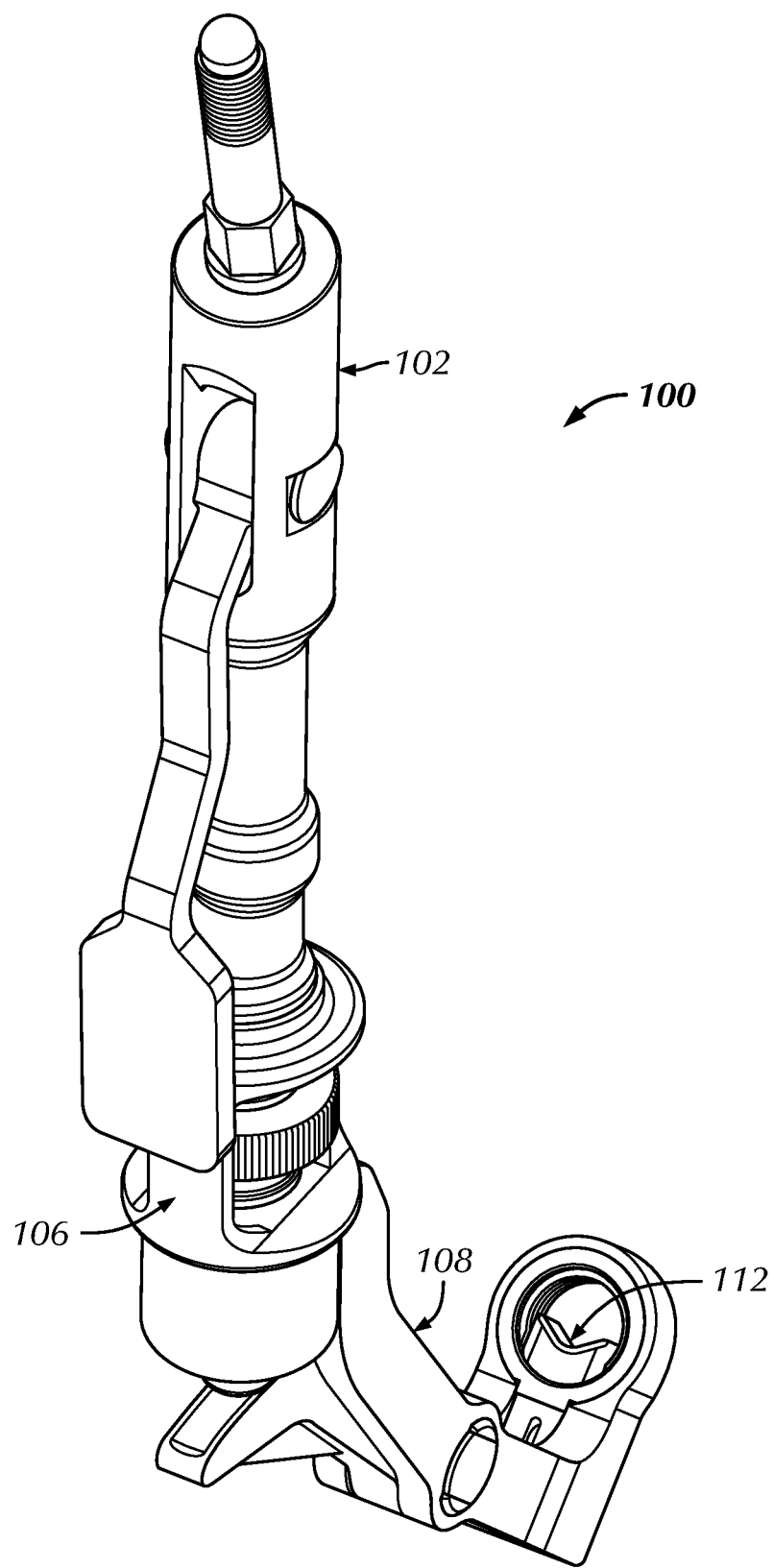
FIG. 5 is a top perspective view of the implant extractor of FIG. 1.

As shown in FIGS. 2, 4 and 5, the jaw 112 extends from a distal end of the support arm 108. According to an aspect, the jaw 112 is a sliding jaw. In particular, the jaw 112 is slidingly received in a channel 184 of the jaw carrier 180 (FIGS. 16B, 16C and 16E). The jaw assembly includes a central passageway having a longitudinal axis "$L_J$" (FIG. 2)

substantially parallel to the longitudinal axis of the support arm. The central passageway is defined by an opening 186 (FIGS. 16B and 16C) in the jaw carrier 180 for receiving an implant e.g., a trunnion 116 of a hip stem implant 118 (FIG. 1). According to an aspect, a wall of the opening 186 can be provided with grip-enhancing structure such as knurling or the like or a plurality of ribs or teeth (FIG. 5). However, as described below in connection with FIGS. 19A-19C, the implant extractor preferably includes a gripping insert 188 configured to be received in the central passageway of the jaw carrier.

Figure 18:
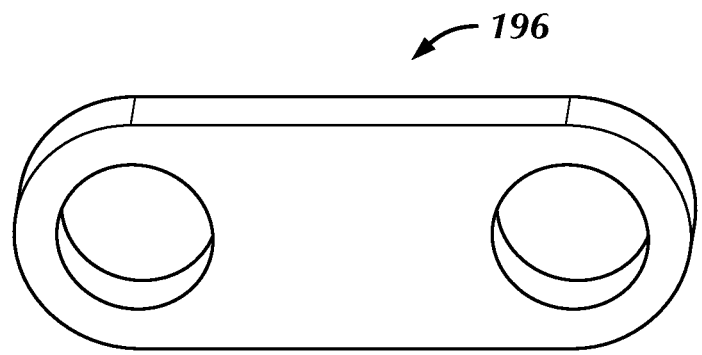
FIG. 18 is a perspective view of a link connecting the rocker arm and jaw of the implant extractor of FIG. 1.

The rocker arm 114 is best shown in FIGS. 17A-17C. A proximal end 190 of the rocker arm is constructed and arranged to be contacted by the distal end 138 of the telescoping push rod 104 (FIGS. 1 and 2). A distal end 192 of the rocker arm is bifurcated to define a slot 194 for receiving a first end of a link 196 (FIG. 18), the second end of which is received in a slot 198 of jaw 112 (FIG. 20B). As shown in FIGS. 2 and 4, pins 200 and 202 respectively retain the distal end of the rocker arm to the link 196 and the link to jaw 112. As best shown in FIGS. 17B and 17C, the distal end 192 of the rocker arm has a recess 203 to facilitate installation and removal of pin 200 from the link 196. Further, the rocker arm has a lower arm segment "$d_2$" (FIG. 2) of about 10 to 100 mm, including 20, 30, 40, 50, 60, 70, 80, 90, 110 and 120 mm, and an upper arm segment "$d_1$" (FIG. 2) of about 50 to 400 mm, including 40, 60, 70, 80, 90, 100, 120, 140, 160, 180, 200, 220, 240, 260, 280, 300, 320, 340, 360, 380, 400 and 420 mm. The rocker arm ratio can be determined by $d_1/d_2$. According to the subject disclosure, the rocker arm 114 has a rocker arm ratio of about 1.5:1 to 8:1, including 1.0:1, 2.0:1, 3.0:1, 4.0:1, 5:0:1, 6.0:1, 7.0:1 and 9.0:1.

Figure 19A:
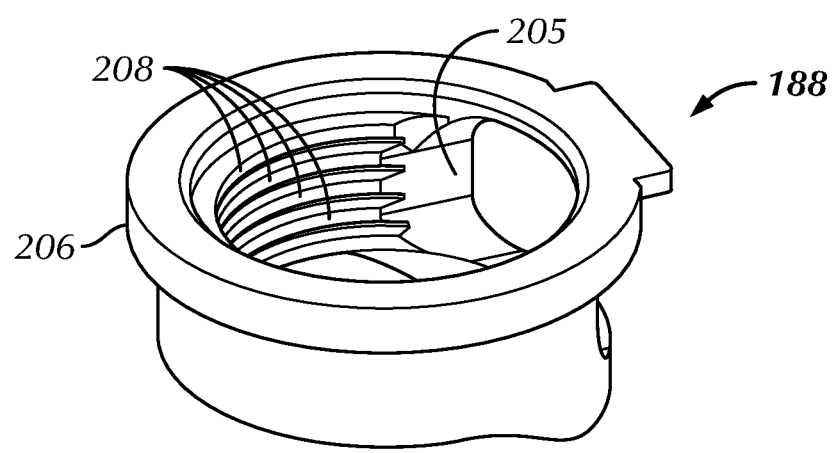
FIG. 19A is a front perspective view of an insert for receiving a jaw of the implant extractor of FIG. 1.
Figure 19B:
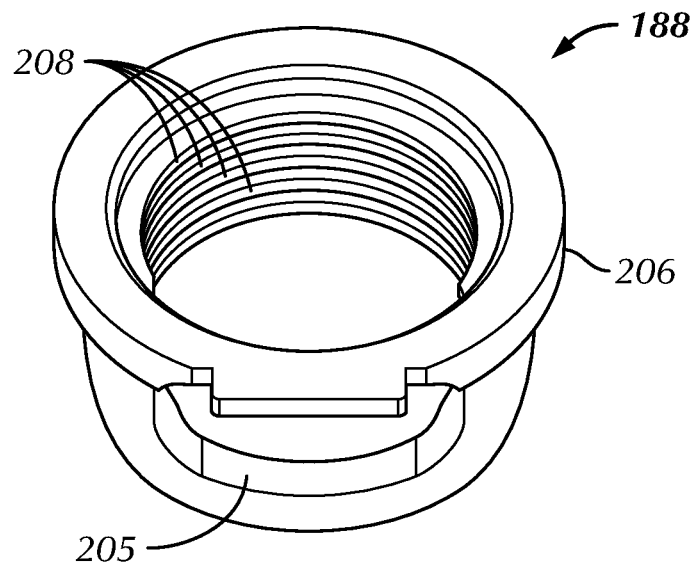
FIG. 19B is a rear perspective view of the insert of FIG. 19A.
Figure 19C:
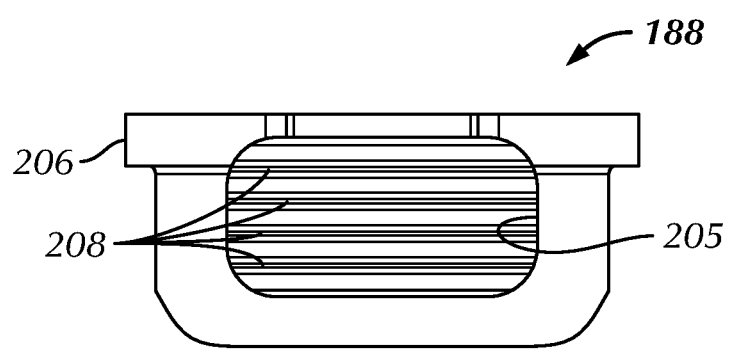
FIG. 19C is a rear view of the insert of FIG. 19A.

Referring to FIGS. 19A-19C, there is shown the gripping insert 188 configured to be received in the central passageway of the jaw carrier. As described below, the gripping insert 188 and the jaw 112 cooperate to tightly grip e.g., a hip stem implant trunnion 116. The gripping insert is annular in shape with a lateral opening 205 for receiving the jaw 112, whereby the jaw retains the insert within the central passageway when the jaw is received in the lateral opening. In addition, the insert preferably includes a radially projecting annular flange 206 which is configured to be seated within a cooperating annular recess 207 provided in a distal end of the jaw carrier 180 (FIGS. 16B and 16C). The insert further includes grip-enhancing structure 208 that aligns with the jaw when the insert is received within the central passageway. By way of example, but not limitation, the grip-enhancing structure 208 may comprise knurling or the like or, as illustrated, a plurality of ribs or teeth. The grip-enhancing structure cooperates with grip-enhancing structure provided on the distal face of the jaw 112, described below, to firmly grip e.g., the trunnion of a hip implant.

Figure 3:
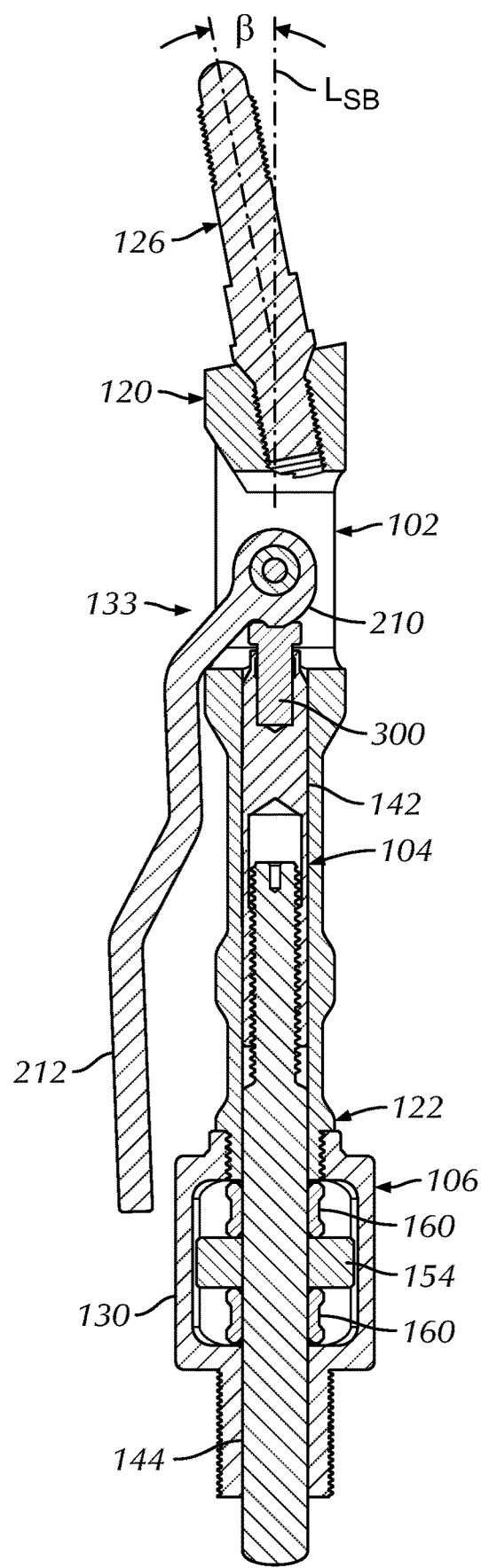
FIG. 3 is a side cross-sectional view of an upper portion of the implant extractor of FIG. 1.

As shown in FIGS. 2 and 3, the implant extractor 100 further comprises the cam lock 133 operatively engaged with the telescoping push rod 104. As shown in these figures as well as FIG. 9, the cam lock includes a cam 210 housed within the shaft body for engaging a proximal end of the telescoping push rod, and a lever 212 extending from the cam. More specifically, the cam lock 133 is positioned above the telescoping push rod such that the cam operatively engages a proximally facing or top surface of the telescoping push rod.

As shown in FIGS. 1-3 and 8, the implant extractor further comprises the tool connector 126. The tool connector extends laterally away from the shaft body 102 substantially opposite from the direction the support arm 108 extends laterally away from the shaft body. According to an aspect, the tool connector extends laterally away from the longitudinal axis of the shaft body at an angle "β" (FIG. 3) of about 12 to 15 degrees, including 10, 11, 13, 14, 16, 18 and 20 degrees. The tool connector 126 has a threaded distal end 214 for threadedly engaging the internally threaded opening 124 at the proximal end of the shaft body. In addition, the tool connector has a threaded proximal end 216 for threadedly engaging a tool including, for example and without limitation, an extraction handle such as a C-frame (FIGS. 24A and 24B), and a polygonal, e.g., octagonal, midsection 217 for engagement with another tool. Alternatively, the polygonal midsection can assume any other shape that is readily engageable by a tool e.g., a wrench, including, without limitation, square and hexagonal.

Figure 20A:
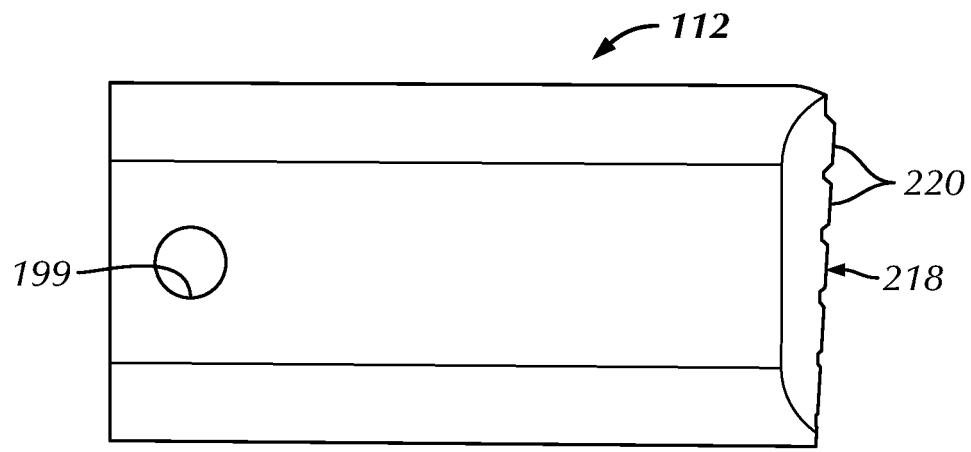
FIG. 20A is a side view of the jaw of the implant extractor of FIG. 1 in accordance with a first exemplary embodiment.
Figure 20B:
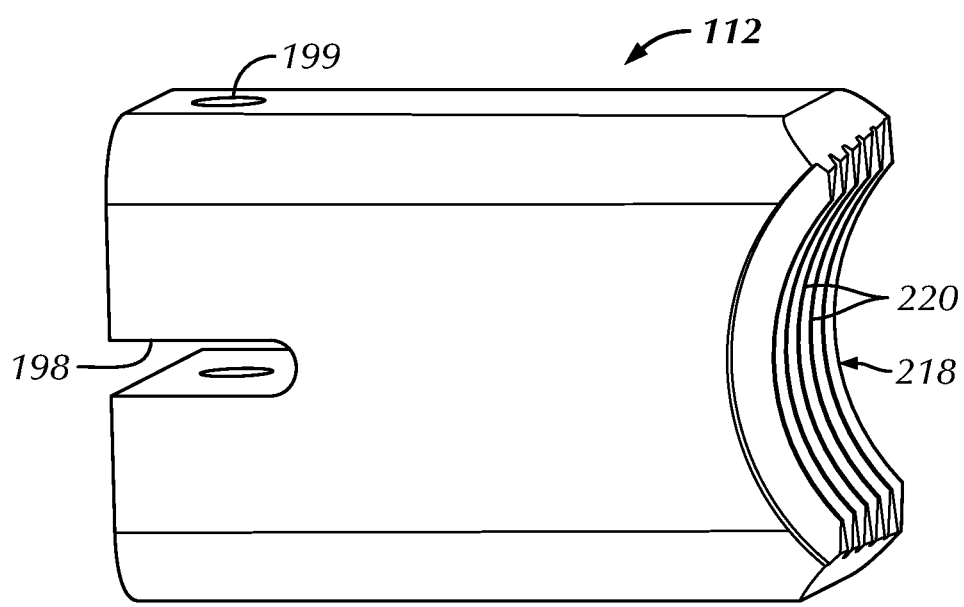
FIG. 20B is a top perspective view of the jaw of FIG. 20A.

Referring to FIGS. 20A and 20B, there is shown a first exemplary embodiment of the jaw 112 of the implant extractor 100. At its forward face 218 the jaw 112 includes grip-enhancing structure 220 such as knurling or the like or, as illustrated, a plurality of ribs or teeth. Like the ribs 208 of the insert 188, the ribs or teeth 220 of the jaw can be disposed substantially horizontally. Further, the forward face 218 is substantially concave. At its rearward end the jaw is provided with the slot 198 for receiving the second end of the link 196. In addition, the rearward end of the jaw is provided with a transverse through hole 199 for receiving the pin 202 in order to retain the link to the jaw.

Figure 21A:
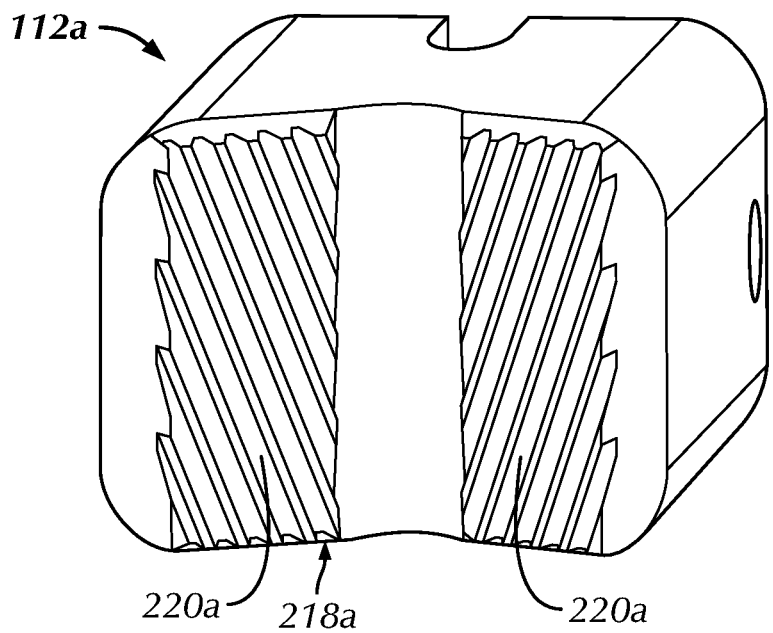
FIG. 21A is a front perspective view of the jaw of the implant extractor of FIG. 1 in accordance with a second exemplary embodiment.
Figure 21B:
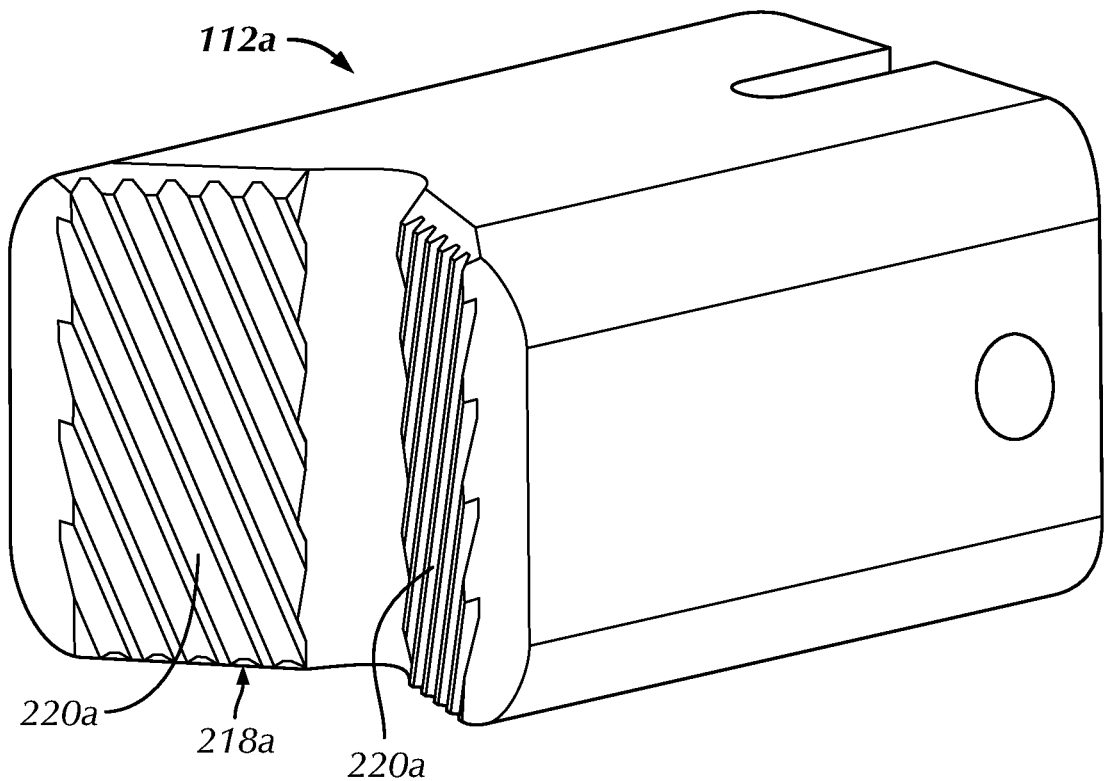
FIG. 21B is a side perspective view of the jaw of FIG. 21A.

Referring to FIGS. 21A and 21B, there is shown a second exemplary embodiment of the jaw 112a of the implant extractor 100. At its forward face 218a the jaw 112a includes grip-enhancing structure 220a such as a plurality of ribs or teeth. The ribs or teeth of the jaw 112a can be disposed substantially diagonally. Further, the forward face 218a is substantially V-shaped to increase the surface area of the ribs or teeth in contact with e.g., the trunnion 116 of the hip stem implant 118.

Figure 22A:
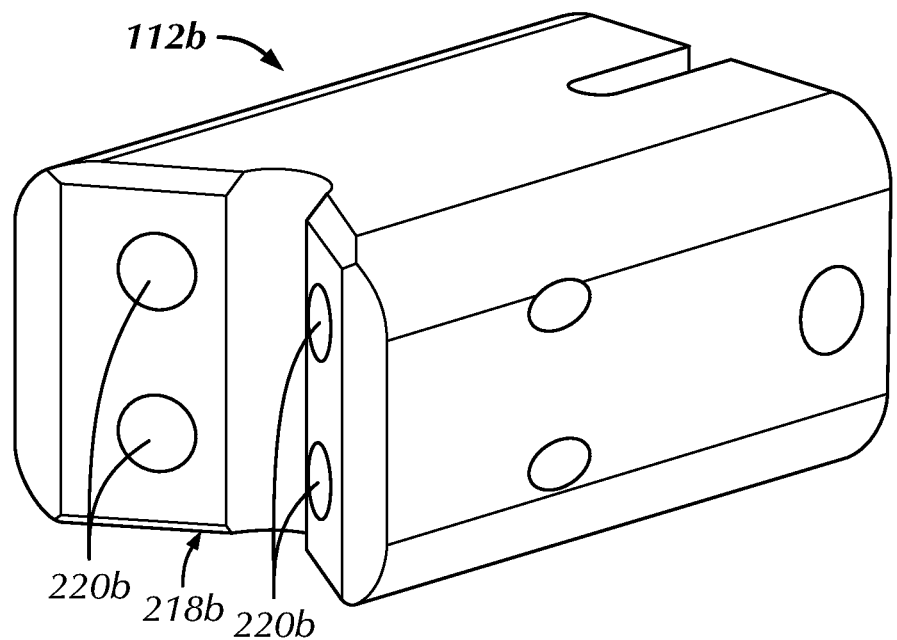
FIG. 22A is a side perspective view of the jaw of the implant extractor of FIG. 1 in accordance with a third exemplary embodiment.
Figure 22B:
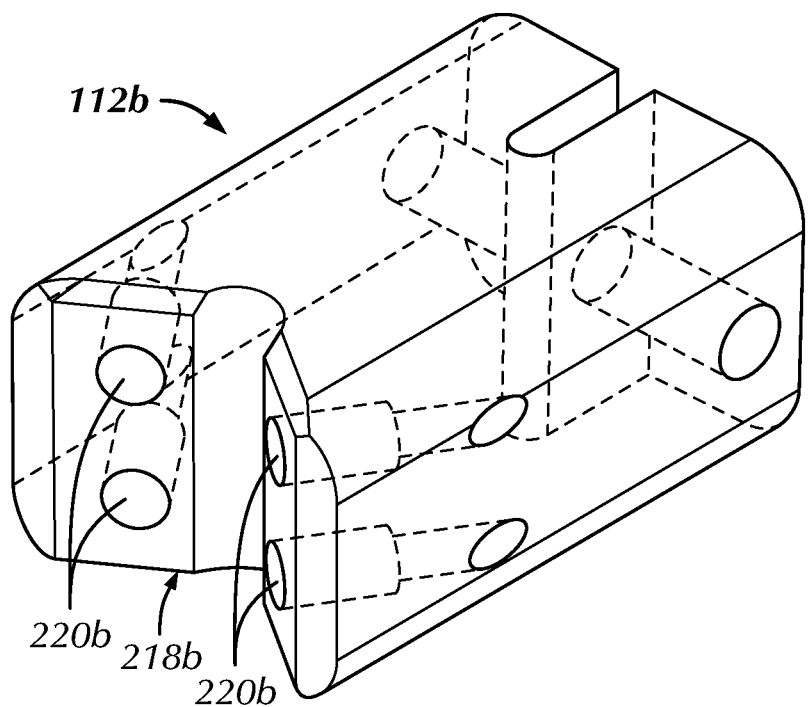
FIG. 22B is a side perspective view of the jaw of FIG. 22A.

Referring to FIGS. 22A and 22B, there is shown a third exemplary embodiment of the jaw 112b of the implant extractor 100. At its forward face 218b the jaw 112b includes grip enhancing structure 220b such as a plurality of hardened pins. Preferably, the pins 220b are replaceable so that they can be changed when damaged. Further, the forward face 218b is substantially V-shaped.

Figure 23A:
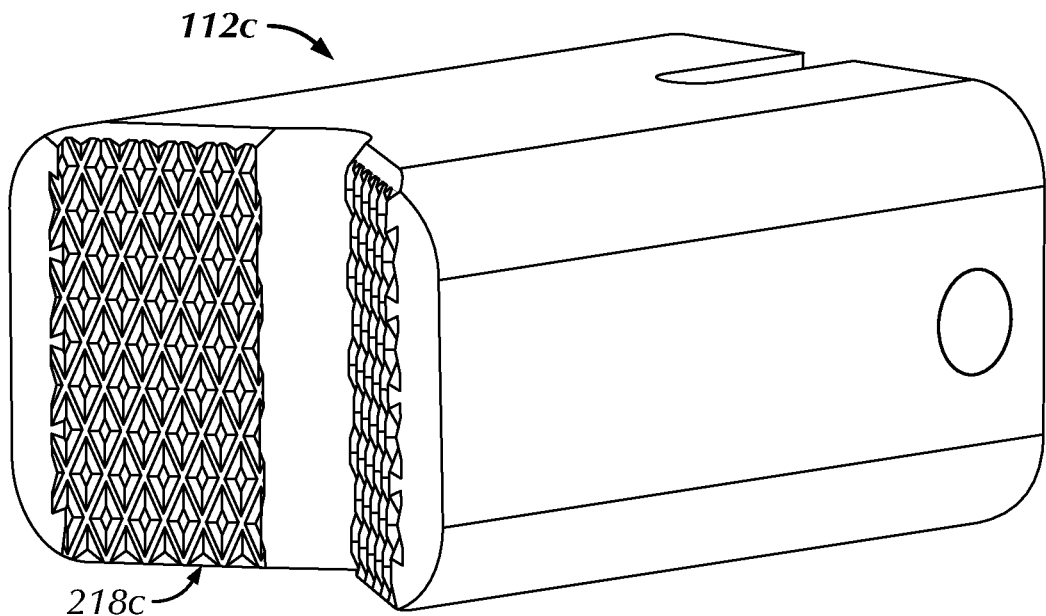
FIG. 23A is a side perspective view of the jaw of the implant extractor of FIG. 1 in accordance with a fourth exemplary embodiment.
Figure 23B:
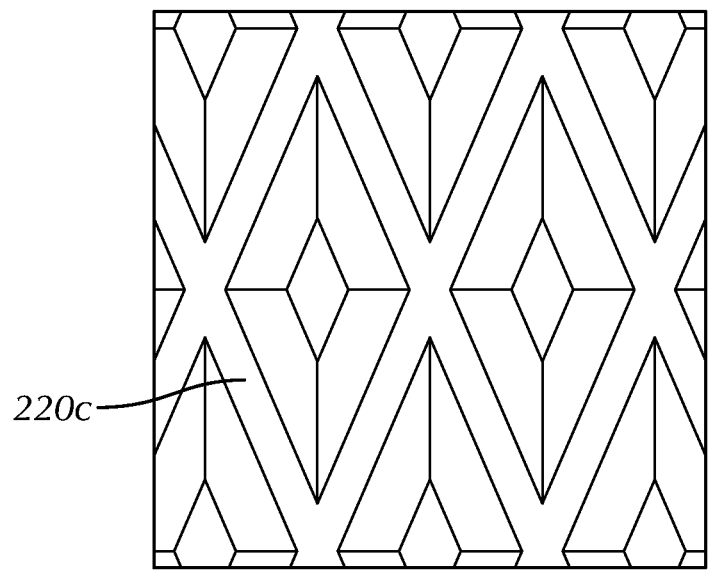
FIG. 23B is a partial enlarged view of the jaw face of the jaw of FIG. 23A.

Referring to FIGS. 23A and 23B, there is shown a fourth exemplary embodiment of the jaw 112c of the implant extractor 100. At its forward face 218c the jaw 112c includes grip enhancing structure 220c such as an array of raised diamond-shaped formations. The height of the diamond-shaped formations is greater than the width thereof for increased grip strength and to reduce the likelihood of shearing e.g., the trunnion 116 of the hip stem implant 118. The forward face 218c can be substantially V-shaped to increase the surface area of the diamond-shaped formations with e.g., the trunnion of the hip stem implant.

Figure 8:
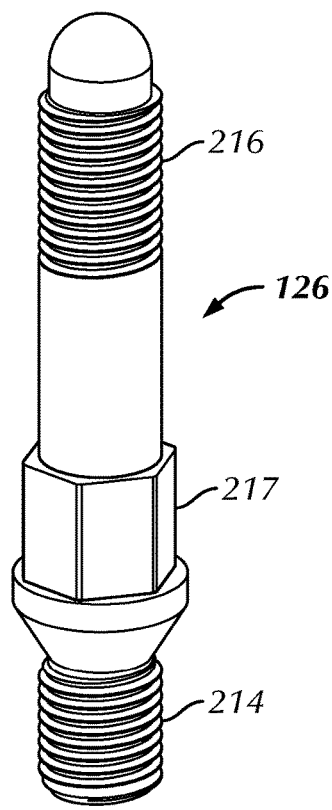
FIG. 8 is perspective view of a tool connector of the implant extractor of FIG.
Figure 9:
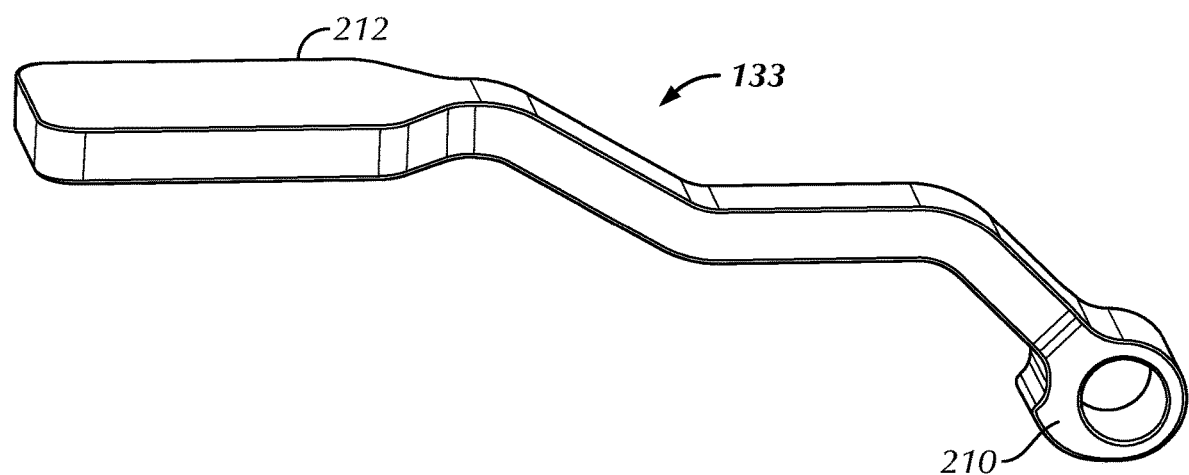
FIG. 9 is a perspective view of a cam lever of the implant extractor of FIG. 1.
Figure 24A:
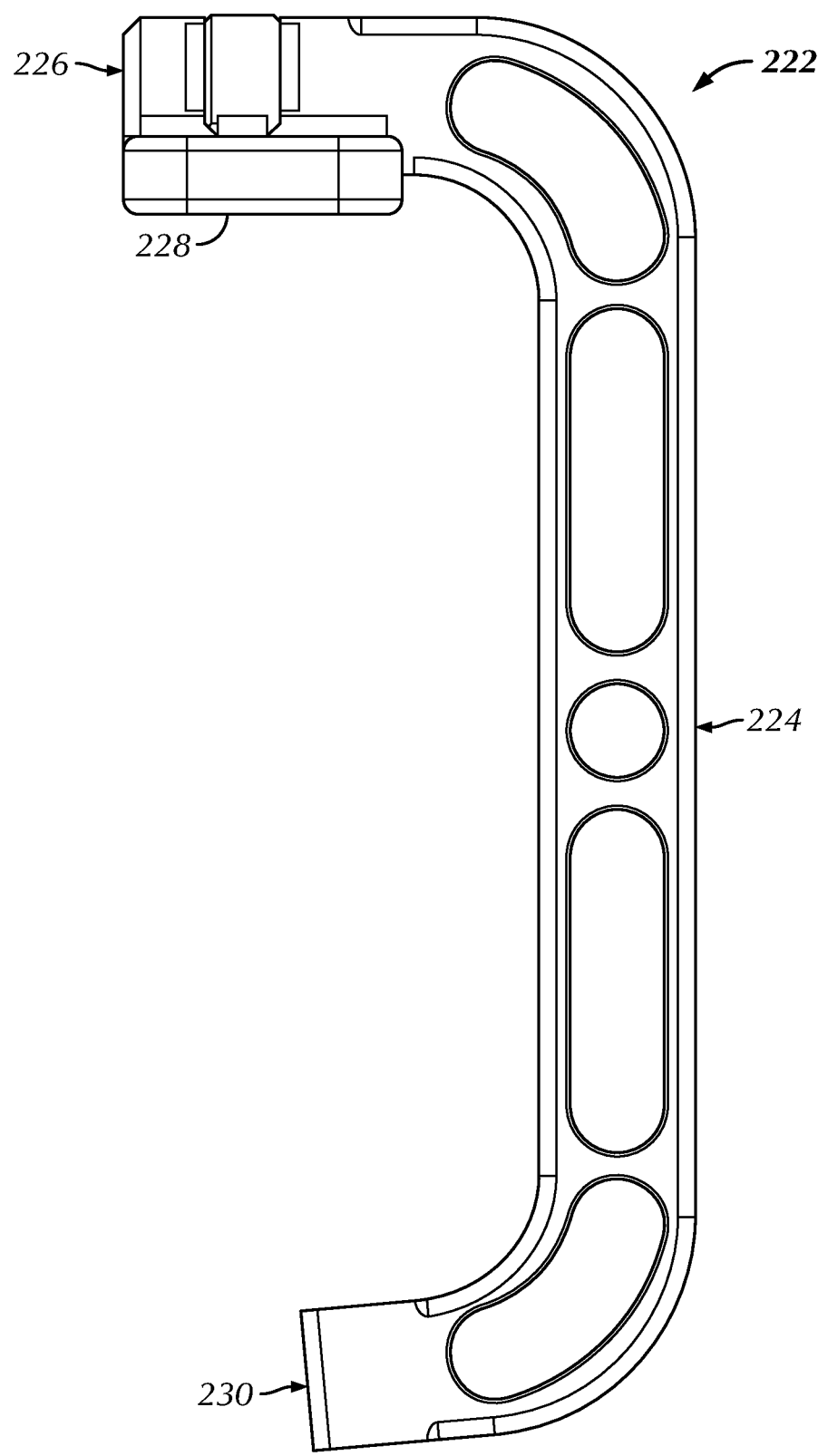
FIG. 24A is a side view of a tool connectable to the implant extractor of FIG. 1.
Figure 24B:
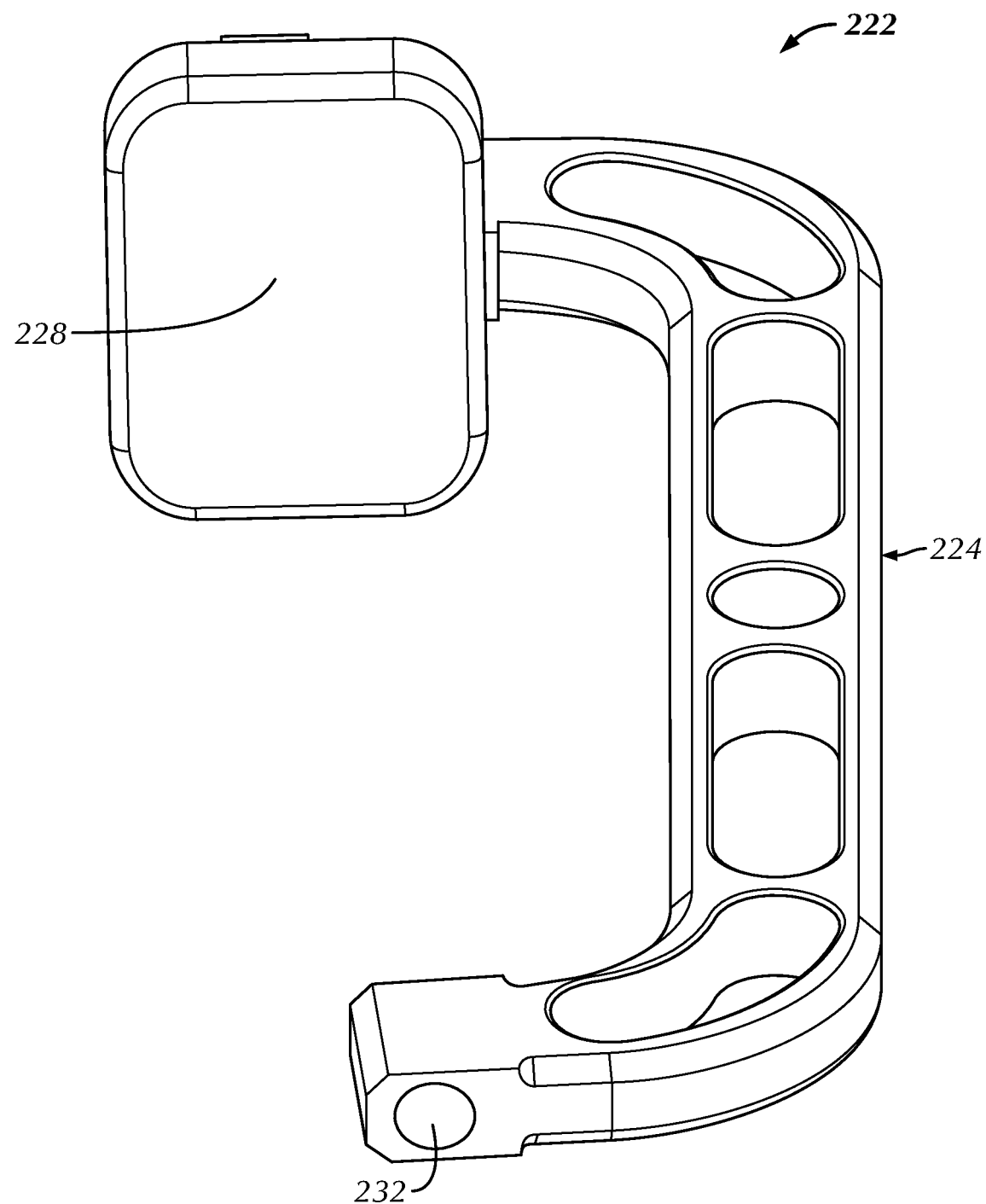
FIG. 24B is a bottom perspective view of the tool of FIG. 24A.

FIGS. 24A and 24B illustrate an exemplary tool, e.g., a C-frame extension handle 222 that can be attached to the tool connector 126 of FIG. 8. The C-frame extension handle includes a generally C-shaped frame 224 having a proximal end 226 to which is secured a strike plate 228. The C-shaped frame further includes a distal end 230 having an internally threaded opening 232 for threadedly receiving the threaded proximal end 216 of the connector tool 126 (FIG. 8) to connect the C-frame extension handle 222 to the connector tool and, thus, the implant extractor 100.

The process of using the implant extractor 100 to remove an implant e.g., a hip stem implant 118 from bone, is as follows. Initially, a user e.g., a surgeon, retracts the jaw 112 a sufficient distance whereby the jaw carrier opening 186 may receive the hip stem implant trunnion 116. Retraction of the jaw 112 is achieved by rotating the adjustment knob 154 in a first direction, thereby causing the distal end 138 of the telescoping push rod 104 to retract within the shaft body. More particularly, rotation of the adjustment knob in the first direction causes the distal rod segment 144 of the telescoping push rod to thread into the proximal rod segment 142 thereof, thereby shortening the length of the telescoping push rod. As the adjustment knob is rotated, it is restrained from axial movement in the adjustor cage 130 by spacers 160 contacting opposite faces of the adjustment knob and the adjustor cage. Thus, as the adjustment knob is rotated in a first direction, the distal rod segment 144 slides upwardly relative to the adjustment knob. Simultaneously, the proximal rod segment is prevented from rotating by virtue of pin 136 (which is anchored to the shaft body 102 at the through bore 134) contacting the planar surface 150 of the proximal rod segment.

With the distal end 138 of the telescoping push rod 104 sufficiently retracted, the rocker arm can be pivoted clockwise (when viewed as shown in FIG. 2) relative to the support arm 108 (FIGS. 1, 2 and 4) to withdraw the jaw 112 from obstructing the jaw carrier opening 186. At this point, the jaw carrier opening can be placed over the hip stem implant trunnion 116 until the jaw carrier surrounds the trunnion. Thereafter, the user rotates the adjustment knob 154 in a second direction opposite the first direction. This causes the distal rod segment 144 of the telescoping push rod 104 to extend from the proximal rod segment 142 and the distal end 138 of the telescoping push rod to press downwardly on the proximal end 190 of the rocker arm, whereby the rocker arm pivots counter clockwise (when viewed as shown in FIG. 2) relative to the support arm 108. Concurrently, the distal end 192 of the rocker arm pushes the sliding jaw 112 into contact with the hip stem implant trunnion 116. The user continues to turn the adjustment knob in the second direction until the ribs or teeth 220 of the jaw face 218 and the corresponding ribs or teeth 208 of the insert 188 firmly grip the hip stem implant trunnion. With the trunnion firmly gripped, the user moves the cam lock lever 212 from the unlocked position shown in FIG. 6 to the locked position shown in FIGS. 1-3, whereby the cam 210 presses downwardly on the proximal end of the telescoping push rod 104 which causes further downward displacement of the telescoping push rod corresponding to the height of the cam. Consequently, the distal end 138 of the telescoping push rod moves downwardly thereby moving the proximal end of the rocker arm to cause additional clockwise rotation of the rocker arm. This, in turn, forces the distal end of the rocker arm to drive the jaw 112 into clamping engagement with the trunnion. Owing to the cam lock lever, the significant strength of the rocker arm, and the rocker arm ratio, the implant extractor advantageously provides very high clamping forces on the hip implant trunnion. For example, due to the sizing and construction of the lever arm, the implant extractor can impart clamping load forces of between about 1000 to 1200 pounds (4448 to 5337 Newtons) on the hip implant trunnion. Such high clamping forces are necessary as conventional extractors oftentimes fail due to insufficient clamping on the hip implant trunnion. Additionally, a substantially stiff, yet resilient plug 300, e.g., a polymeric plug (FIGS. 2 and 3) can be provided near the proximal end of the proximal push rod segment 142 to permit the cam lock lever 212 to move from the unlocked to locked positions when the adjustment knob is firmly hand tightened.

With the trunnion clamped between the jaw face and the ribs or teeth 208 of the insert 188, the user pulls upwardly on the implant extractor. If pulling upwardly on the implant extractor is insufficient to extract the hip stem implant from surrounding bone, the user can attach the C-frame 222 to the tool connector 126. Thereafter, the user strikes the strike plate 228 with a hammer, mallet or similar striking tool until the implant is dislodged.

With the implant removed from the bone, the user can extract the implant from the implant extractor by moving the cam lock lever 212 from the locked position shown in FIGS. 1-3 to the unlocked position shown in FIG. 6. The user can then pull on the implant. If the implant does not loosen from pulling alone, then the user can rotate the adjustment knob 154 in the first direction until the jaw 112 disengages from the trunnion, whereby the user can easily free the implant from the jaw carrier.

Owing to the angled extension of the tool connector relative to the shaft body, and the extension angle of the support arm from the shaft body, e.g., through the angle of the tool connector being opposite that of the extension angle of the support arm, impact or removal forces from the implant extractor on the hip stem results in reduced moment or rotational forces on the hip implant.

So constructed, the main shaft of the implant extractor is laterally spaced from the jaw assembly advantageously allowing for the implant extractor to get around the belly of a patient due to the anterior approach employed and to provide needed space for, e.g., a C-frame extension handle. Further, the present implant extractor advantageously has all of its controls outside of the incision area of a patient to facilitate ease of implant extractor operation. Furthermore, the telescoping push rod advantageously allows for greater operational flexibility of the device thereby allowing for use on different size trunnions. Additionally, the link is constructed and laid out such that it carries no loads (except compression forces) from the rocker arm during use or engagement of the implant extractor on a hip implant.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

We claim:

1. An implant extractor comprising:
   a shaft body;
   a telescoping push rod extending from the shaft body, the telescoping push rod including a proximal rod segment and a distal rod segment moveable relative to the proximal rod segment;
   an adjustor engaged with the push rod for adjusting a length of the telescoping push rod;
   a support arm extending laterally from the shaft body; and
   a jaw assembly extending from the support arm, the jaw assembly including:
      a jaw moveable between a locking position and an unlocking position, and
      a rocker arm operatively engaged with the push rod and the jaw.

2. The implant extractor of claim 1, further comprising a cam lock operatively engaged with the telescoping push rod.

3. The implant extractor of claim 2, wherein the cam lock includes a cam housed within the shaft body, and a lever extending from the cam.

4. The implant extractor of claim 1, wherein the telescoping push rod is housed within the shaft body.

5. The implant extractor of claim 4, wherein a distal end of the telescoping push rod extends past a distal end of the shaft body.

6. The implant extractor of claim 1, wherein the telescoping push rod is moveable relative to the shaft body.

7. The implant extractor of claim 1, wherein the telescoping push rod includes a distal rod segment having a planar side.

8. The implant extractor of claim 1, wherein the telescoping push rod includes a proximal rod segment having a rotation limiter.

9. The implant extractor of claim 1, wherein the adjustor is positioned about a distal end of the shaft body.

10. The implant extractor of claim 1, wherein the adjustor includes an adjustment knob engaged with the telescoping push rod.

11. The implant extractor of claim 1, wherein the support arm extends from a distal end of the adjustor.

12. The implant extractor of claim 1, wherein the support arm has a longitudinal axis that extends from a longitudinal axis of the shaft body at an angle of about 100 to 170 degrees.

13. The implant extractor of claim 1, wherein the support arm has a length of about 10 to 400 mm.

14. The implant extractor of claim 1, wherein the jaw extends from a distal end of the support arm.

15. The implant extractor of claim 1, wherein the jaw is a sliding jaw.

16. The implant extractor of claim 1, wherein the jaw assembly includes a central passageway having a longitudinal axis substantially parallel to a longitudinal axis of the support arm.

17. The implant extractor of claim 16, further comprising a gripping insert configured to be received in the central passageway.

18. The implant extractor of claim 17, wherein the gripping insert includes grip-enhancing structure.

19. The implant extractor of claim 17, wherein the gripping insert is annular with a lateral opening for receiving the jaw.

20. The implant extractor of claim 1, wherein the rocker arm is pivotably connected to the support arm.

21. The implant extractor of claim 1, wherein the rocker arm has a rocker arm ratio of about 1.5:1 to 8:1.

22. The implant extractor of claim 1, wherein the rocker arm has at least one arm of about 10 to 100 mm.

23. The implant extractor of claim 1, further comprising a tool connector extending laterally from the shaft body in a direction substantially opposite from the direction the support arm is extending laterally from the shaft body.

24. An implant extractor comprising:
a shaft body;
a tool connecter extending laterally away from a proximal end of the shaft body;
a telescoping push rod mounted within and extending from the shaft body, the telescoping push rod including a proximal rod segment and a distal rod segment moveable relative to the proximal rod segment;
a cam lock mounted within the shaft body for engaging a proximal end of the telescoping push rod;
an adjustor mounted to a distal end of the shaft body, the adjustor including an adjustment knob engaged with the telescoping push rod for adjusting a length of the telescoping push rod;
a support arm mounted to a distal end of the adjustor and extending laterally away from the shaft body; and
a jaw assembly extending from a distal end of the support arm, the jaw assembly including:
a jaw moveable between a locking position and an unlocking position, and
a rocker arm mounted to the support arm and operatively engaged with the telescoping push rod and the jaw.

* * * * *